(12) United States Patent
Davis et al.

(10) Patent No.: US 6,448,400 B1
(45) Date of Patent: Sep. 10, 2002

(54) SELF-ASSEMBLED IONOPHORES

(75) Inventors: Jeffrey T. Davis, College Park; Sampath K. Tirumala, Greenbelt, both of MD (US); Allison L. Marlow, Madison, WI (US)

(73) Assignee: The University of Maryland at College Park, College Park, MD (US)

( * ) Notice: Subject to any disclaimer, the term of this patent is extended or adjusted under 35 U.S.C. 154(b) by 0 days.

(21) Appl. No.: 09/380,585

(22) PCT Filed: Mar. 11, 1998

(86) PCT No.: PCT/US98/04334

§ 371 (c)(1),
(2), (4) Date: Nov. 24, 1999

(87) PCT Pub. No.: WO99/07372

PCT Pub. Date: Feb. 18, 1999

Related U.S. Application Data

(60) Provisional application No. 60/040,284, filed on Mar. 11, 1997.

(51) Int. Cl.$^7$ .......................... C07D 473/34; C07F 1/00
(52) U.S. Cl. ........................ 544/225; 534/10; 544/230; 544/276; 588/236
(58) Field of Search .............................. 544/230, 276, 544/225; 534/10; 588/236

(56) References Cited

PUBLICATIONS

Davis et al., Journal of Organic Chemistry, vol. 60, No. 13, pp. 4167–4176, Jun. 30, 1995.*

* cited by examiner

*Primary Examiner*—Richard L. Raymond
(74) *Attorney, Agent, or Firm*—Oblon, Spivak, McClelland, Maier & Neustadt, P.C.

(57) ABSTRACT

Ionophores having the capacity spontaneously assemble in solution and composed of hydrogen bonded monomers of 5'-(t-butyl-dimethylsilyl)-2',3'-O-isopropylidene-isoguanosine, 5'-(t-butyl-dimethylsilyl)-2',3'-O-isopropylidene-thio-isoguanosine or 2',3'-Di-O-acetyl-5'-(t-butyl-dimethylsilyl)-isoguanosine are used to remove 137-cesium ions ($^{137}Cs^+$) from nuclear waste.

49 Claims, 23 Drawing Sheets

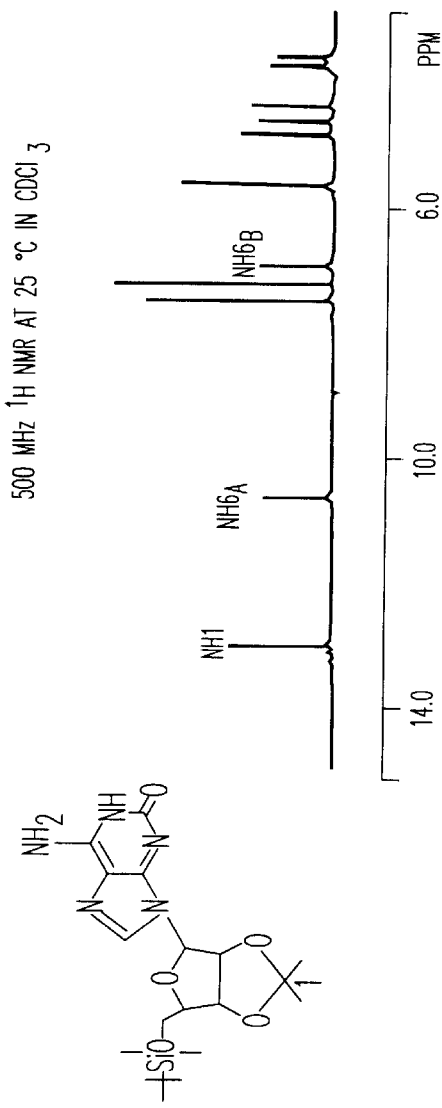
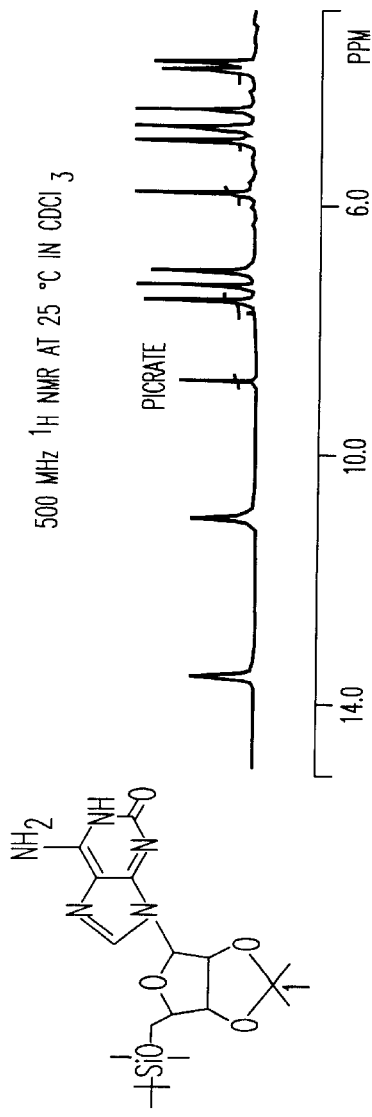
FIG. 9A
FIG. 9B

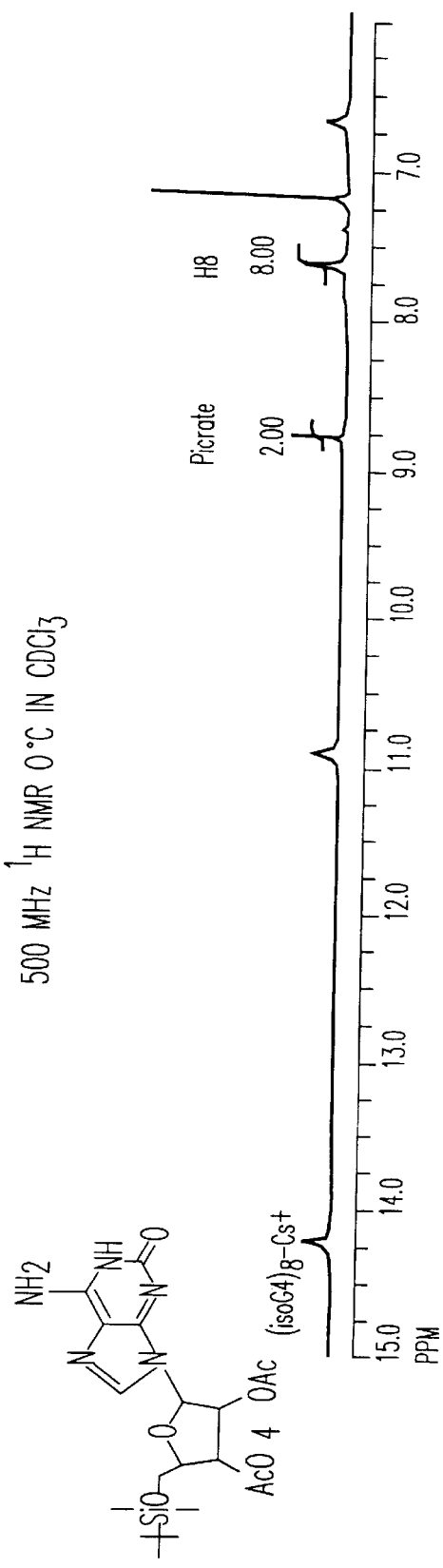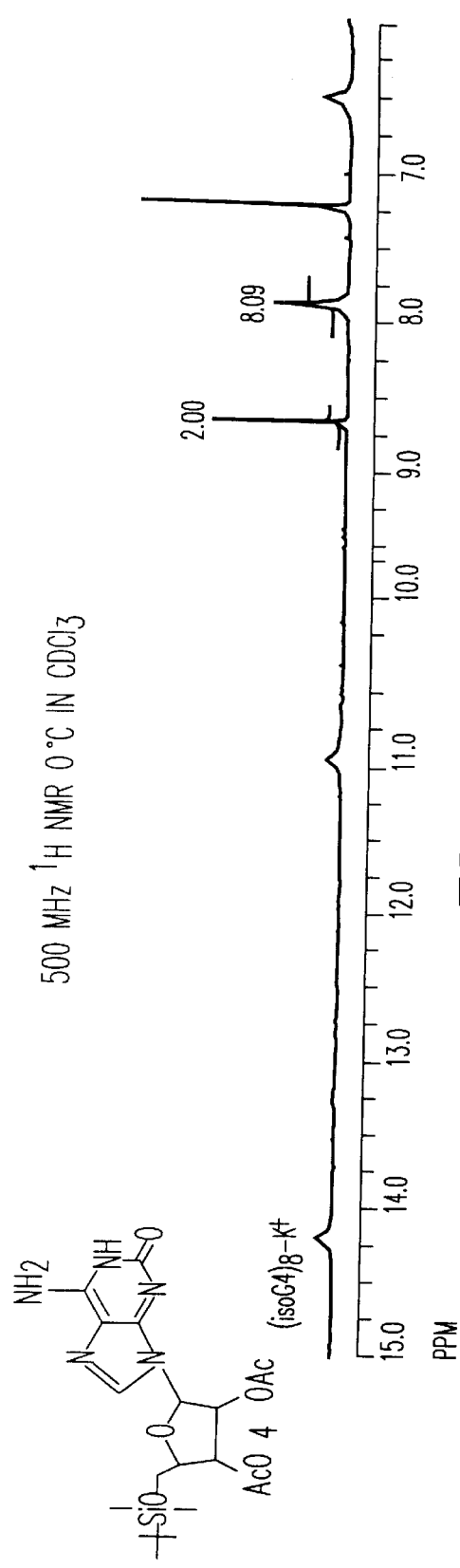
FIG. 10A
FIG. 10B

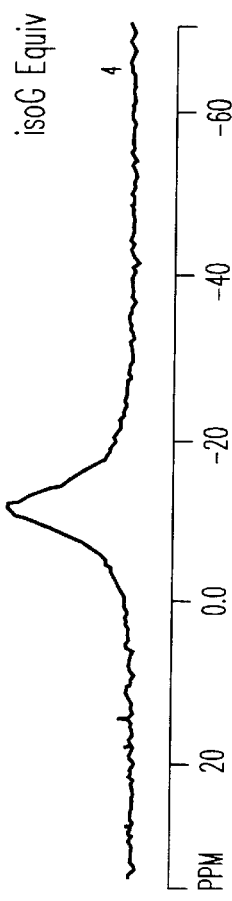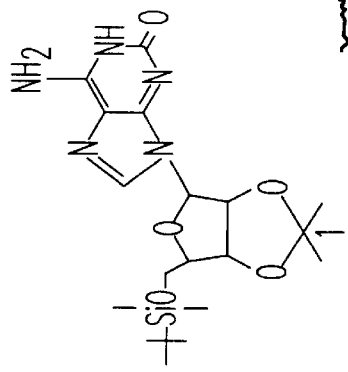
FIG. 13B
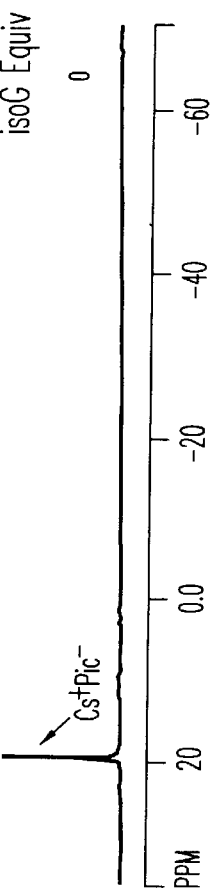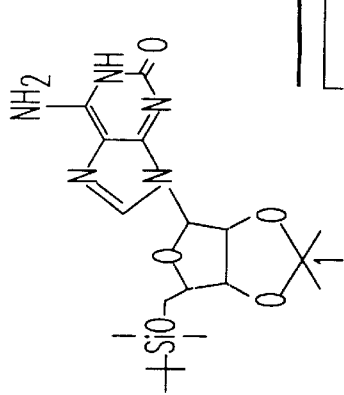
FIG. 13A

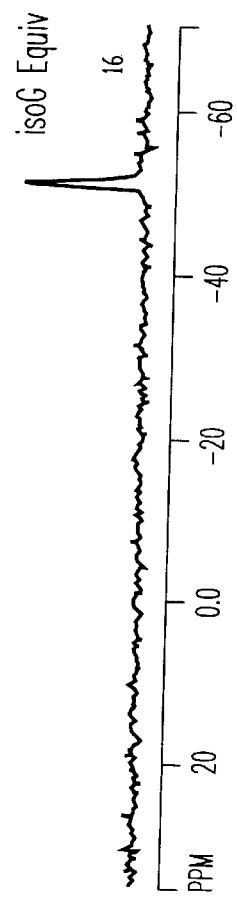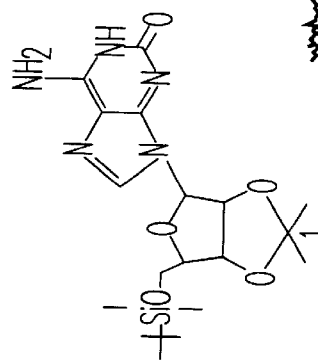
FIG. 13D
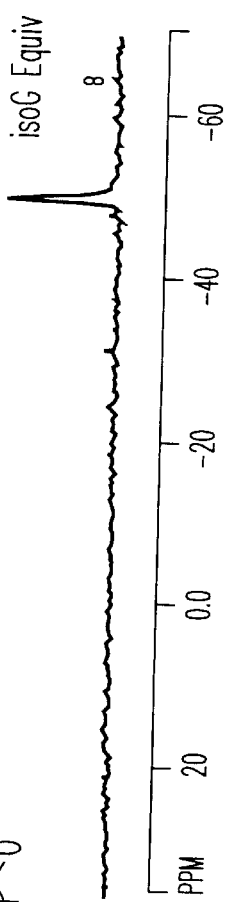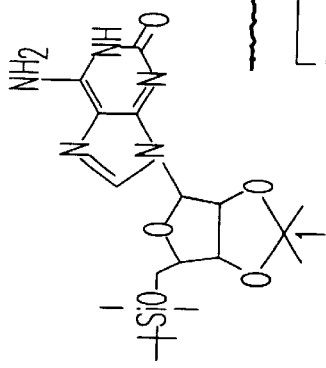
FIG. 13C

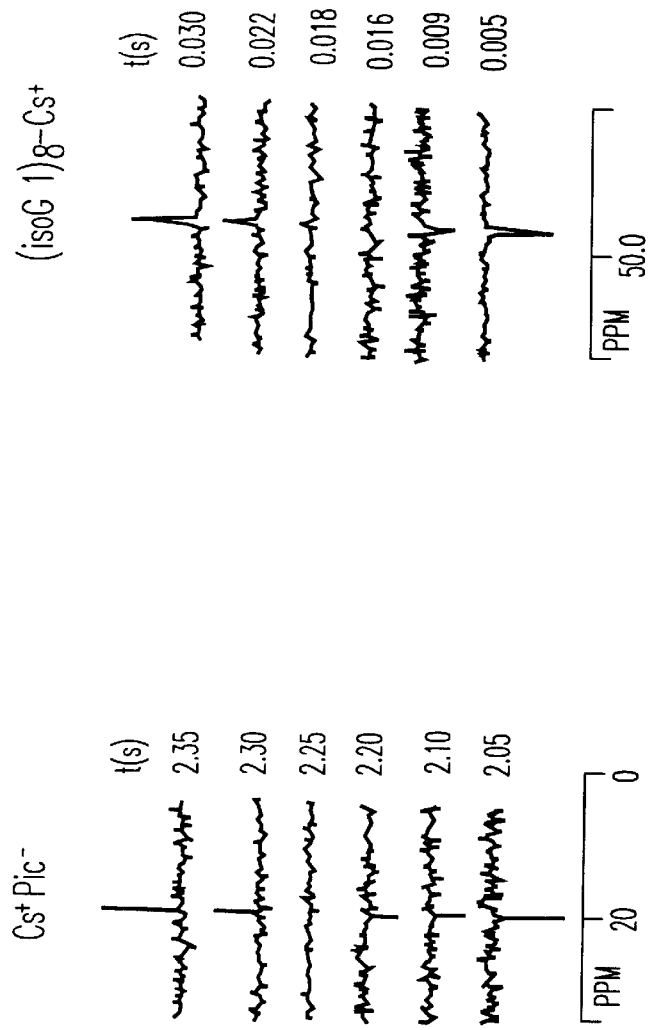

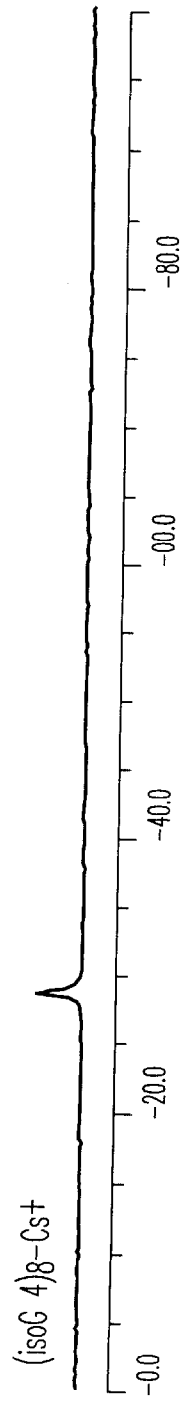
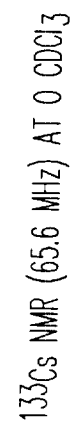
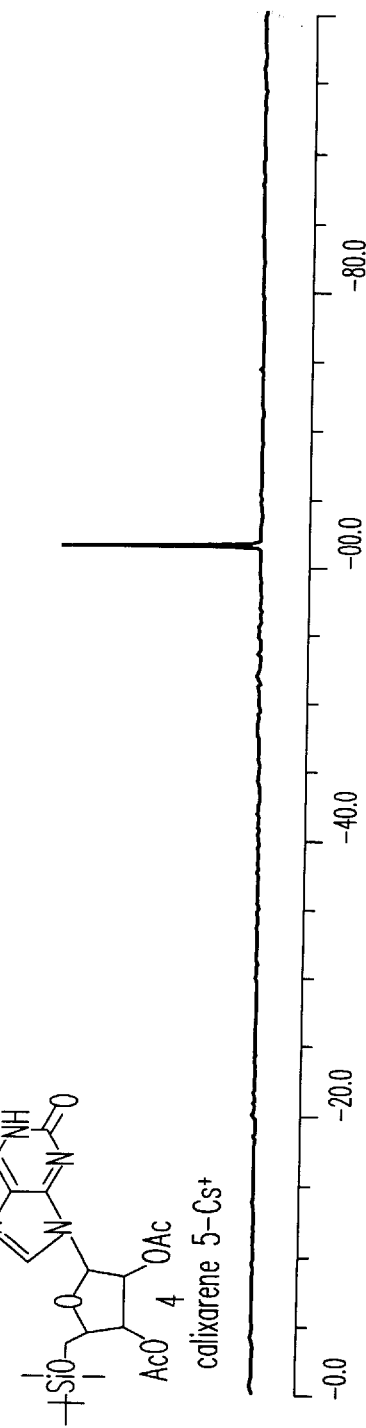
FIG. 15A
FIG. 15B

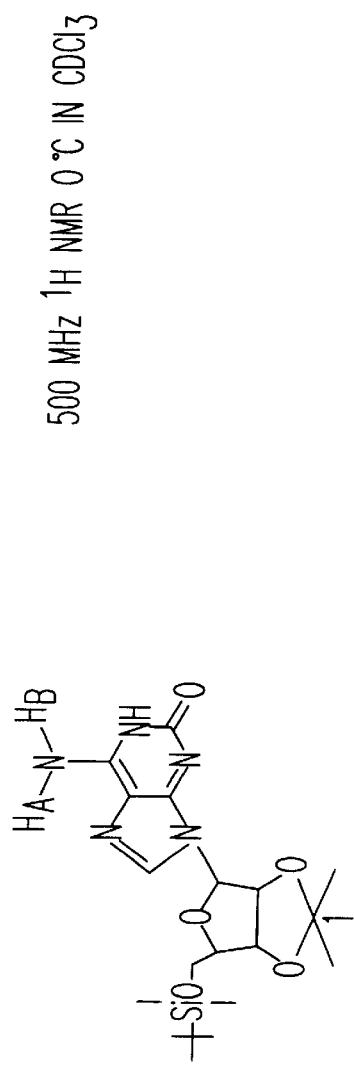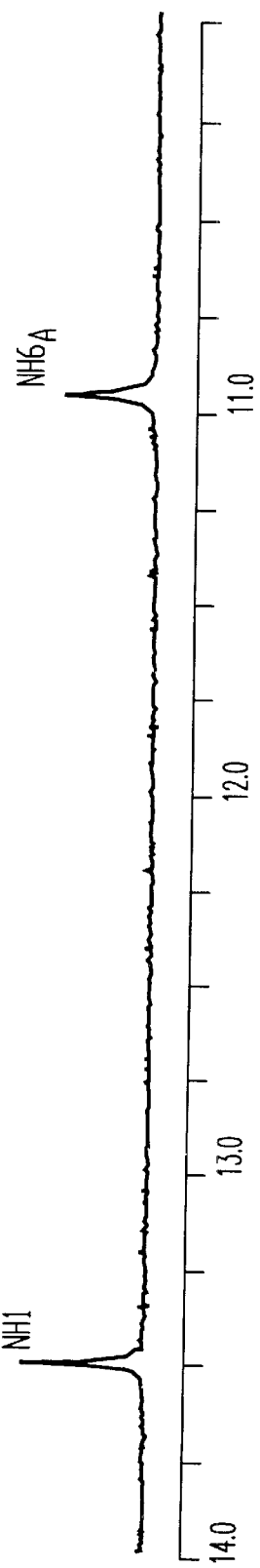
FIG. 16A

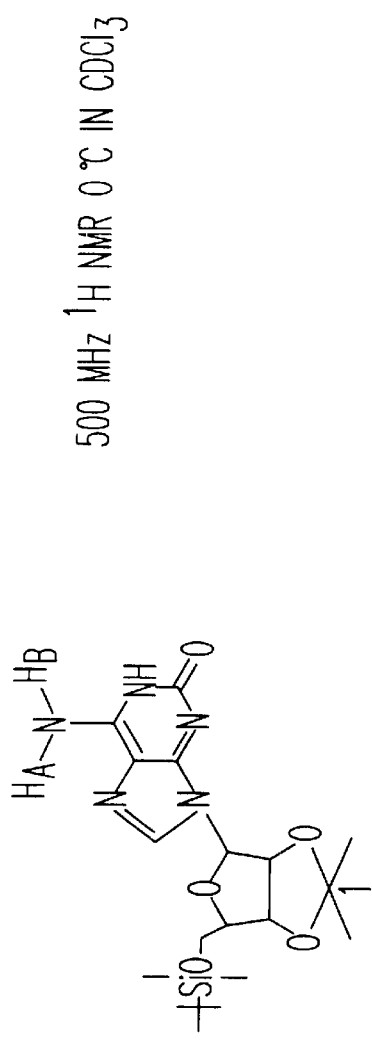
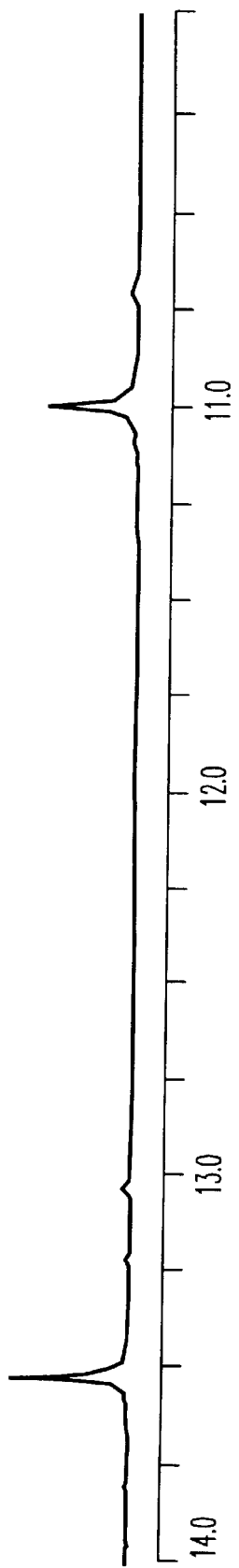
FIG. 16B

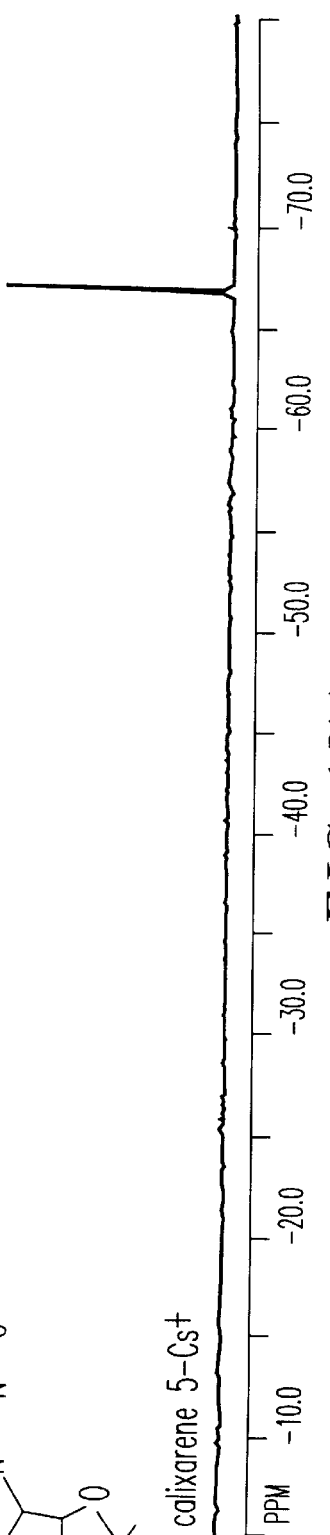
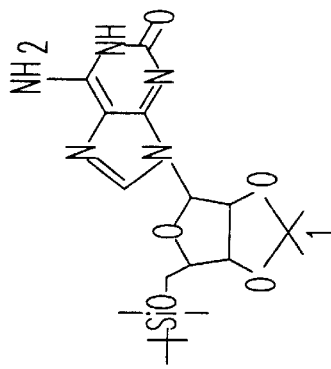
FIG. 17A
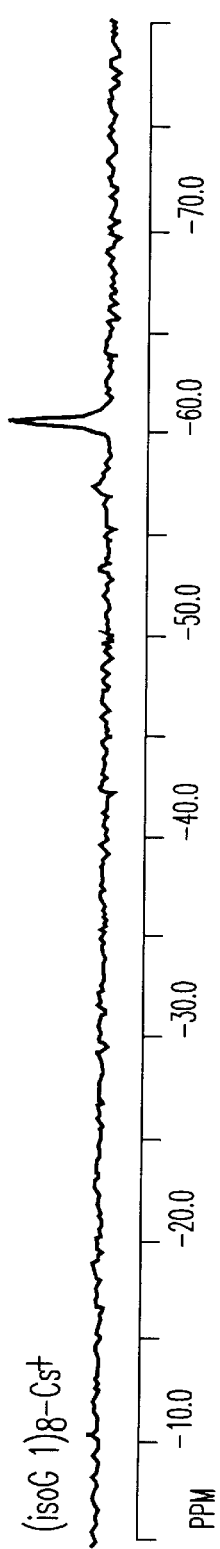
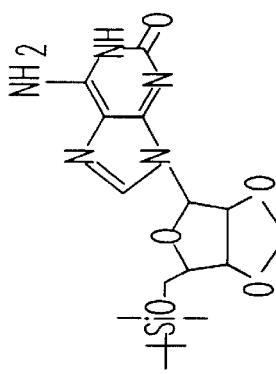
FIG. 17B

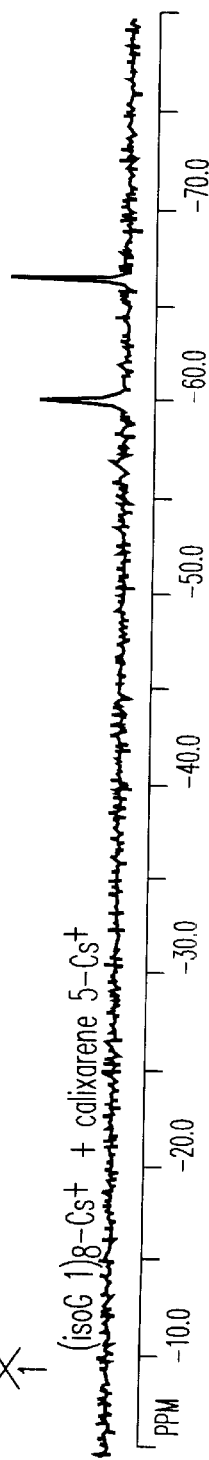
$^{133}$Cs NMR (65.6 MHz) AT 0 °C CDCl$_3$
FIG. 17C
(isoG 1)$_8$–Cs$^+$ + calixarene 5–Cs$^+$
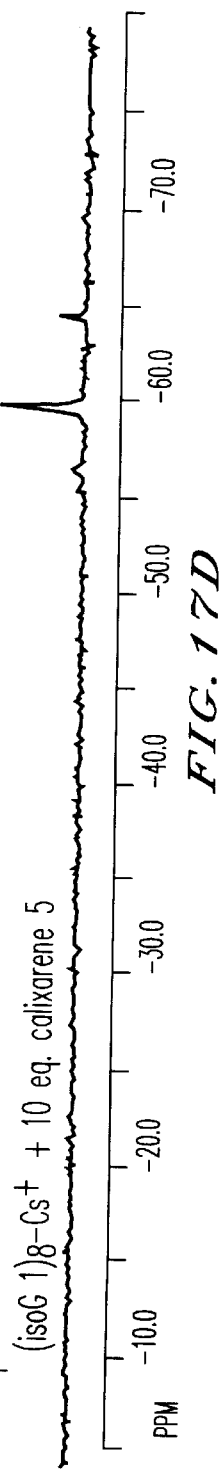
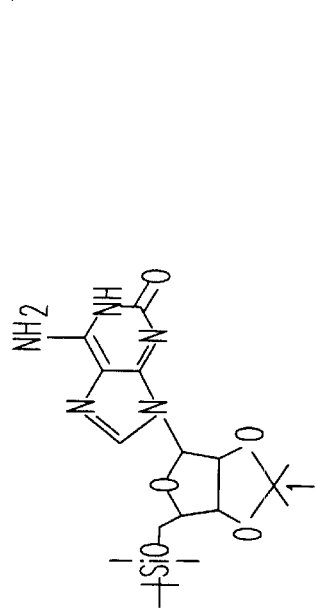
$^{133}$Cs NMR (65.6 MHz) AT 0 °C CDCl$_3$
FIG. 17D
(isoG 1)$_8$–Cs$^+$ + 10 eq. calixarene 5

SELF-ASSEMBLED IONOPHORES

This application is a 371 of PCT/US98/04334, filed Mar. 11, 1998, and entitled to the right of priority of U.S. Provisional Application Serial No. 60/040,284 filed on Mar. 11, 1997, the entire contents of which are herein incorporated by reference.

BACKGROUND OF THE INVENTION

1. Field of the Invention

The present invention relates to ionophores which have the capacity to spontaneously assemble in solution. More particularly, the present invention concerns ionophore composed of hydrogen-bonded monomers of 5'-(t-butyl-dimethylsilyl)-2',3'-O-isopyoidene-isoguanosine, or 5'-(t-butyl-dimethylsilyl)-2',3'-O-isopropylidene-thio-isoguanosine, and use of these ionophores for removing 137-cesium ions ($^{137}Cs^+$) from nuclear waste.

2. Description of the Related Art

The United States faces a crisis in nuclear waste management. Safety and health issues surrounding nuclear waste have caused considerable interest in methods for separating radioactive isotopes[4,5,9] Cesium-137 ($^{137}Cs^+$) is a major product from uranium fission. Due to its 30 year half-life, much of the $^{137}Cs^+$ produced during the nuclear age still exists. $^{137}Cs^+$ and $^{90}Sr$ are the major heat sources in radioactive waste at Hanford Nuclear Reservation. Different methods for $^{137}Cs^+$ removal and/or recovery from nuclear waste have been described, including selective precipitation as phospho-tungstate salts, inorganic ion exchanges, and solvent extraction using crown ethers.[4,5] Since the $Na^+$ concentration in nuclear waste is $10^3$–$10^4$ times that of $^{137}Cs^+$, ionophores with high $Cs^+/Na^+$ selectivity are required to separate $^{137}Cs^+$ from nuclear waste.

There are few $Cs^+$-selective ionophores known. Due to its large size, selective extraction of $Cs^+$ (r=1.67 Å) from solutions containing $Na^+$ (r=0.97 Å) and $K^+$ (r=1.33 Å) is challenging. Initially, design of $Cs^+$ ionophores relied on large-ring crown ethers. Specifically, 21-c-7 and 23-c-8 have been proposed as ionophores for $^{137}Cs^+$ extractions.[6] The use of large-ring crown ethers poses special challenges because of their flexibility. Thus, both the $Cs^+$ binding constants and $Cs^+$ selectivities of large-ring crown ethers are relatively modest.[10] Better results have been obtained using rigid macrocycles, such as calixarenes.[7,12-14] While their $Cs^+$ binding constants and $Cs^+/K^+$ selectivities are often impressive, these rigid ionophores have two major problems: 1) they are difficult to synthesize and are available only in small quantities; and 2) due to high association constants, cation recovery from the ionophore complex is difficult.

SUMMARY OF THE INVENTION

The present invention solves the problems noted above by providing an ionophore useful for removing $^{137}Cs^+$ from nuclear waste. The term "ionophore" as used herein refers to molecule or an assembly of molecules which either has the capacity to bind one or more ions, or is actually bound to one or more ions. The ionophore of the present invention comprises a plurality of monomers, wherein each monomer is noncovalently bound to another monomer, preferably through hydrogen bonding. Ideally, the ionophore is capable of spontaneously assembling in a solution containing the plurality of monomers. These inophores self-assemble at concentrations as low as 1 μM in $CHCl_3$ or $CH_3CN$. The ionophore advantageously comprises identical monomers such as 5'-(t-butyl-dimethylsilyl)-2',3'-O-isopropylidene-isoguanosine, 5'-(t-butyl-dimetlhylsilyl)-2',3'-O-isopropylidene-thio-isoguanosine, or 2',3'-Di-O-acetyl-5'-(t-butyl-dimethylsilyl)-isoguanosine. The ionophore may contain four or eight monomers. The ionophore is capable of forming a complex with an ion. This ion is preferably a cation such as $Cs^+$, $Na^+$, $K^+$, $Ag^+$, $Hg^{+2}$, $Pb^{+2}$, or $Cd^{+2}$, preferably $Cs^+$, and most preferably $^{137}Cs^+$. Ideally, the binding affinity of the ionophore for $Cs^+$ is greater than the binding affinity of the ionophore for $Na^+$ or $K^+$. The present invention includes the complex comprising the ionophore and the ion. Also, the present invention includes a micelle comprising a plurality of the ionophores, wherein each monomer comprises a hydrophobic moiety making micelle formation possible, wherein the ion is bound to one of the ionophores of the micelle; the hydrophobic moiety-containing monomer preferably has the following structure:

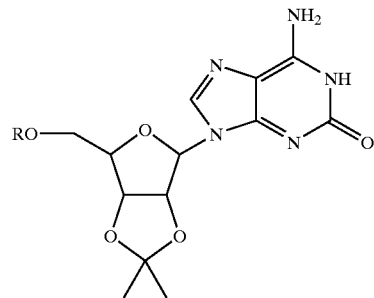

wherein R is H or $—SiR''_3$, where R'' is a hydrocarbon $(CH_2)_m CH_3$ wherein m=0–22, or an ester $C=O(CH_2)_n CH_3$, wherein n=0–22.

Additionally, the present invention is also directed to three methods:

(1) a method for forming the complex comprising the steps of adding the plurality of monomers to a solution containing the ion;

(2) a method for removing the ion from a solution comprising adding the plurality of monomers to the solution, and removing the resultant complex from the solution; and (3) a method for removing the ion from an aqueous solution comprising adding a plurality of the hydophobic moiety-containing monomers to the solution. In method (3), the monomers form a composition comprising a micelle, wherein the micelle is composed of the ionophores, and the ionophores have ions bound thereto. The composition is then removed from the solution, preferably by ultrafiltration.

BRIEF DESCRIPTION OF THE DRAWINGS

FIG. 9 illustrates a region of the 500 MHz $^1$H NMR specurum of 5'-(t-butyl-dimethylsilyl)-2',3'-O-isopropylidene-isoguanosine (isoG 1) (16 mM) in CDCl$_3$ at 25° C. A) Before extraction; B) After extraction with water containing 5 mM cesium picrate. Integration of the picrate signal at a 8.78 ppm and resonances for isopropylidene 1 indicate formation of the octamer, (isoG 1)$_8$-Cs$^+$ picrate.

FIG. 13 illustrates a 65.6 MHz $^{133}$Cs NMR spectra in CD$_3$CN at 25° C.; A) Cesium picrate (10 mM) before titrating of 5'-(t-butyl-dimethylsilyl)-2',3'-O-isopropylidene-isoguanosine (isoG 1); B) After addition of 4 eq. of isoG 1. The limiting chemical shift change indicates that isoG 1 binds Cs$^+$ as an octamer in CD$_3$CN. C) After addition of 8 eq. of isoG 1. D) After addition of 16 eq. of isoG 1.

FIG. 14 illustrates a stack plot of spectra from $^{133}$Cs inversion-recovery T$_1$ experiments in CD$_3$CN at 20° C.; A) Cesium picrate (10 mM). Based on the null point determination, the T$_1$ is 3.25 s; B) For (IsoG 1)$_8$-Cs$^+$ (8 mM). The T$_1$ is 0.0023 s.

FIG. 16 illustrates a region of the 500 MHz $^1$H NMR spectrum for solutions of (isoG 1)$_8$-Cs$^+$ and calixarene 5 in CDCl$_3$ at 0° C.; A) For a solution containing 2 mM (isoG 1)B-Cs$^+$; B) For a solution containing 1.7 mM (isoG 1)$_8$-Cs$^+$ and 17 mM calixarenie 5. Even in the presence of 10 equivalents of calixarene 5 (log K$_a$(Cs$^+$)=8.8) the NH1 peak for (isoG 1)$_8$-Cs$^+$ octamer predominates.

FIG. 17 illustrates a 65.6 MHz $^{133}$Cs NMR spectra in CDCl$_3$ at 0° C.; A) For calixarene 5-Cs$^+$ complex (2.0 mM); B) For (isoG 1)$_8$-Cs$^+$ (2.0) mM); C) For a solution containing a 1:1 mixture of (isoG 1)$_8$-Cs$^+$ (2.0 mM) and calixarene-Cs$^+$ 5 (2.0 mM); D) For a solution containing a 1:10 mixture of (isoG 1-Cs$^+$ (1.7 mM) and calixarene 5 (17 mM). The major $^{133}$Cs resonances corresponds to that for (isoG 1)$_8$-Cs$^+$. There is no evidence for a calixarene-Cs$^+$ peak. There is a small amount of an unknown complex at σ=−58.8 ppm.

DETAILED DESCRIPTION OF THE PREFERRED EMBODIMENTS

Figure 1:
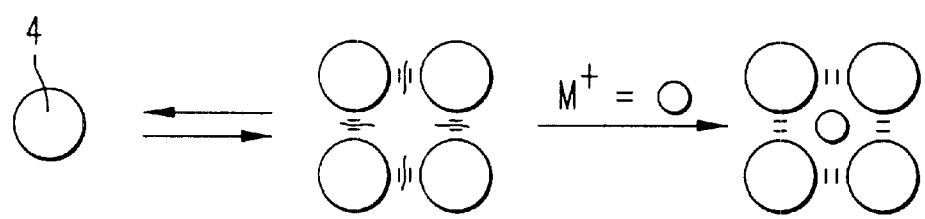
FIG. 1 is a diagram illustrating a self-assembled ionophore, wherein hydrogen bonds form a cation-binding host.
Figure 2:
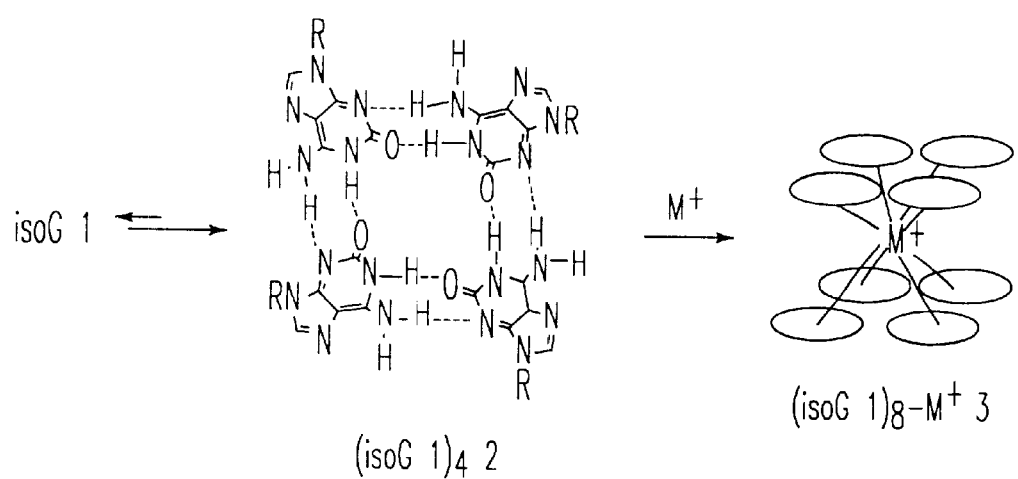
FIG. 2 is a diagram illustrating that in the presence of certain cations, 5'-(t-butyl-dimethylsilyl)-2',3'-O-isopropylidene-isoguanosine (isoG 1) forms an octamer, (isoG 1)$_8$-M$^+$ 3.

The present invention involves a new approach for ion complexation. Ion binding and transport are fundamental to many chemical and biological processes, and thousands of natural and synthetic ionophores are known. Usually, covalent bonds constrain a rigid host into a "preorganized" conformation for productive binding. The novelty of the present invention is in the design of ionophores which self-assemble through noncovalent interactions (see FIG. 1). This alternative ionophore design uses hydrogen bonds to build self-assembled structures that coordinate ions.[15-17] Cation-binding affinity and selectivity may be achieved through cooperative assembly of the host. 5'-(t-butyl-dimethylsilyl)-2',3'-O-isopropylidene-isoguanosine (isoG 1) is the focus of the present invention. IsoG 1 self-associates in organic solvents to form a stable tetramer, (isoG 1)$_4$ 2 (see FIG. 2).[17,18] The tetramer (isoG 1)$_4$ 2, with four oxygens in its central cavity, has a high affinity for cations. IsoG 1 coordinates K$^+$ to form octomer (isoG 1)$_8$-K$^+$ 3, with a binding constant rivaling that of 18-c-6 derivatives.[17b] It is believed that the isopropylidene's conformational rigidity facilitates self-association of isoG 1. The sugar of isoG 1 influences both the Cs$^+$ affinity and Cs$^+$/K$^+$ selectivity of the self-assembled ionophore. Specifically, isoG 1 forms a self-assembled ionophore with remarkable Cs$^+$ selectivity.

One embodiment of the present invention is the use of self-assembled ionophores for environmental applications (e.g., the effective removal of $^{137}$Cs$^+$ from nuclear waste). One of the goals of the present invention, therefore, is to make Cs$^+$ selective self-assembled ionophores. Through an understanding of structural factors that control host association and cation binding, additional self-assembled ionophores that selectively bind and transport cations are developed, such as micellar ionophores for practical Cs$^+$ separations. Organic synthesis is used to prepare a series of structural analogs. Various techniques, including X-ray crystallography, electrospray mass spectrometry, and multi-nuclear NMR spectroscopy are used to determine the structure of the self-assembled ionophores. The self-assembly and cation binding thermodynamics for these isoG 1 analogs is determined using titration calorimetry. Correlation of thermodynamics with structure facilitates design of better self-assembled ionophores. Self-assembled ionophores are used for metal purification, as new materials, and as artificial ion channels.

In the inventive ionophores, self-association via hydrogen bonds results in the formation of a cavity capable of binding cations with high affinity and selectivity. A self-assembled ionophore has two major advantages over covalent ionophores: ease in synthesis, and ease in removal of the cation from the ionophore complex, which should be readily dismantled, allowing the cation and monomer to be separated and recycled.

Certain nucleosides have hydrogen-bonding donor and acceptor groups that allow them to self-associate. IsoG 1 self-assembles to form the tetramer (isoG 1)$_4$ 2 in organic solvents.[1-2] This tetramer, formed by hydrogen bonds, has four nucleophilic oxygen atoms pointing into its central cavity. These oxygen atoms are able to coordinate metal cations. In the presence of certain cations, IsoG 1 forms a remarkably stable octamer, (isoG 1)$_8$-M$^+$ 3 (see FIG. 2). In particular, isoG 1 has an unusually strong affinity and selectivity for Cs$^+$ versus K$^+$ and Na$^+$.[3] The Cs$^+$ binding constants rival those of covalent ionophores, such as crown ethers and cryptands.

Figure 3:
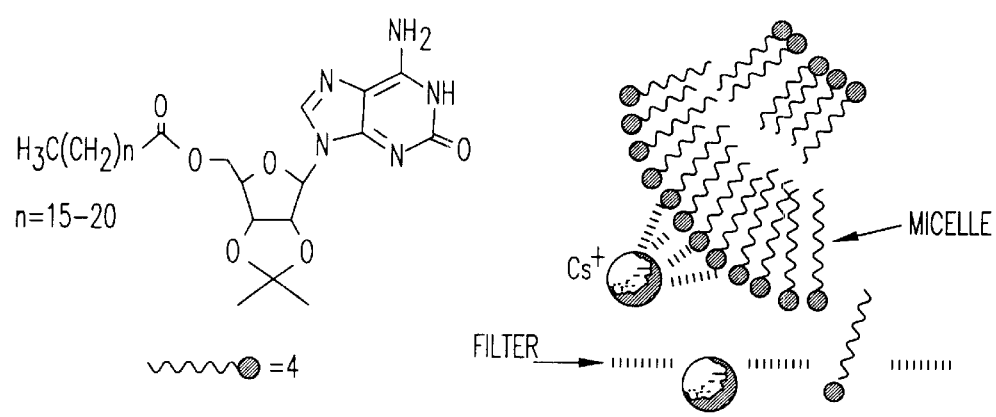
FIG. 3 is a diagram illustrating a micellar ionophore formed by amphiphile 4.

The self-assembled ionophore (isoG 1)$_8$-M$^+$ 3 coordinates metal cations in homogeneous organic solution, and also removes cations from water in liquid-liquid extractions. To overcome the obvious limitations of liquid-liquid extractions, advantage is taken of the unique self-assembly and ion binding properties of isoG 1 to form micelles that will bind Cs$^+$ in water. One potential precursor of these micelles is amphiphile 4, depicted in FIG. 3. By attaching a long-chain alkyl group to the 5'-position of isoG 1, micelles are formed in aqueous solution. Micelles "studded" with the isoG 1 head group form tetramers at the lipid-water interface, and thus coordinate metal cations. Electrostatic interactions at the micellar surface in water are intermediate in strength when compared to the same interactions in water and in the gas phase.[8] Similarly, isoG 1 self-assembly in the micelle is strong enough that coordination of metal cations at the membrane surface is possible. Again, initial experiments focus on the coordination of Cs$^+$ from aqueous solution. As depicted in FIG. 3, Cs$^+$ binding is assayed using an ultrafiltration membrane. Thus, an aqueous solution of Cs$^+$ salts and the micelle result in an equilibrium mixture of salt bound to the micelle. Since the molecular weight of the micelle is large, filtration through a membrane allows only small molecules, such as unbound Cs$^+$ and monomeric amphiphile 4, to pass through the filter. In contrast, any Cs$^+$ bound to the micelle does not pass through the membrane. Measurement of Cs$^+$ concentration, before and after addition of the micelle allows calculation of an equilibrium constant for Cs$^+$ binding. From a practical point of view, the ultrafiltration strategy for metal purification has obvious advantages over liquid-liquid extractions.

Figure 4:
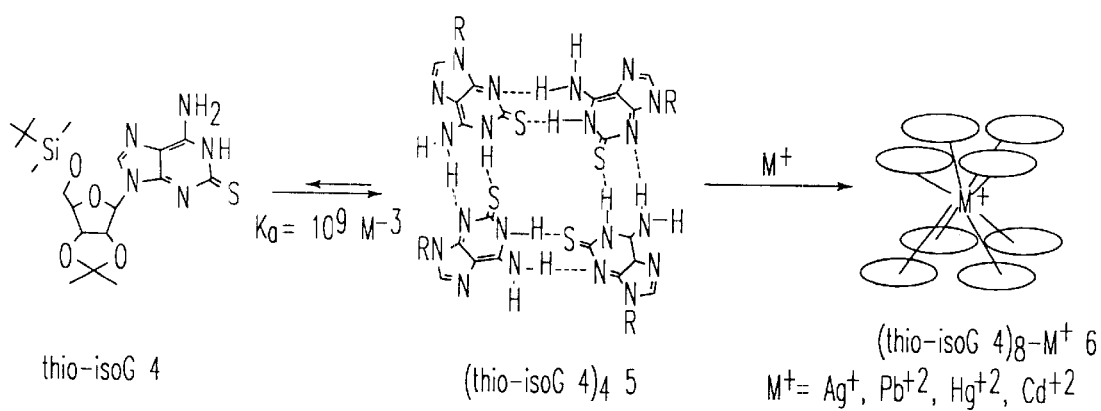
FIG. 4 is a diagram illustrating that in the presence of certain cations, 5'-(t-butyl-dimethylsilyl)-2',3'-O-isopropylidene-thio-isoguanosine (thio-isoG 4) forms an octamer, (thio-isoG 4)$_8$-M$^+$ 6.

Ultimately, self-assembled ionophores with different cavity sizes are made. By varying the cavity size, the ionophore's cation selectivity is changed. Variation of the cavity's hydrogen-bond donors and acceptors is one strategy for tailoring ion selectivity. Models indicate that changing the C2 substituent of isoG 1 from O to S, to give 5'-(t-butyldimethylsilyl)-2',3'-O-isopropylidene-thio-isoguanosine (thio-isoG 4) (see FIG. 4), reduces the tetramer cavity diameter from 2.8–3.0 Å in 2 to 2.1–2.3 Å in tetramer (thio-isoG 4)$_4$ 5. This change favors binding cations with 1.0–1.2 Å radii, rather than the larger cations (1.3–1.5 Å) that coordinate best to the tetramer (isoG 1)$_4$ 2. Also, thiophilic metals will have a higher affinity for tetramer (thio-isoG 4)$_4$ 5 relative to the oxo-containing tetramer (isoG 1)$_4$ 2.

The self-assembly and metal-binding properties of thio-isoG 4 is evaluated. Thiophilic cations organize thio-isoG 4 into higher-ordered structures such as tetramer (thio-isoG 4)$_4$ 5 or octamer (thio-isoG 4)$_8$ 6 (see FIG. 4). Environmentally important cations like Ag$^+$, Hg$^{+2}$, Pb$^{+2}$, and Cd$^{+2}$, all which bind well to sulfur ligands, are particuiarly addressed by these ionophores.[24]

The present invention is illustrated more specifically by referring to the following Example. However, nothing in this example shall be taken as a limitation upon the overall scope of the invention.

EXAMPLE

Figure 5:
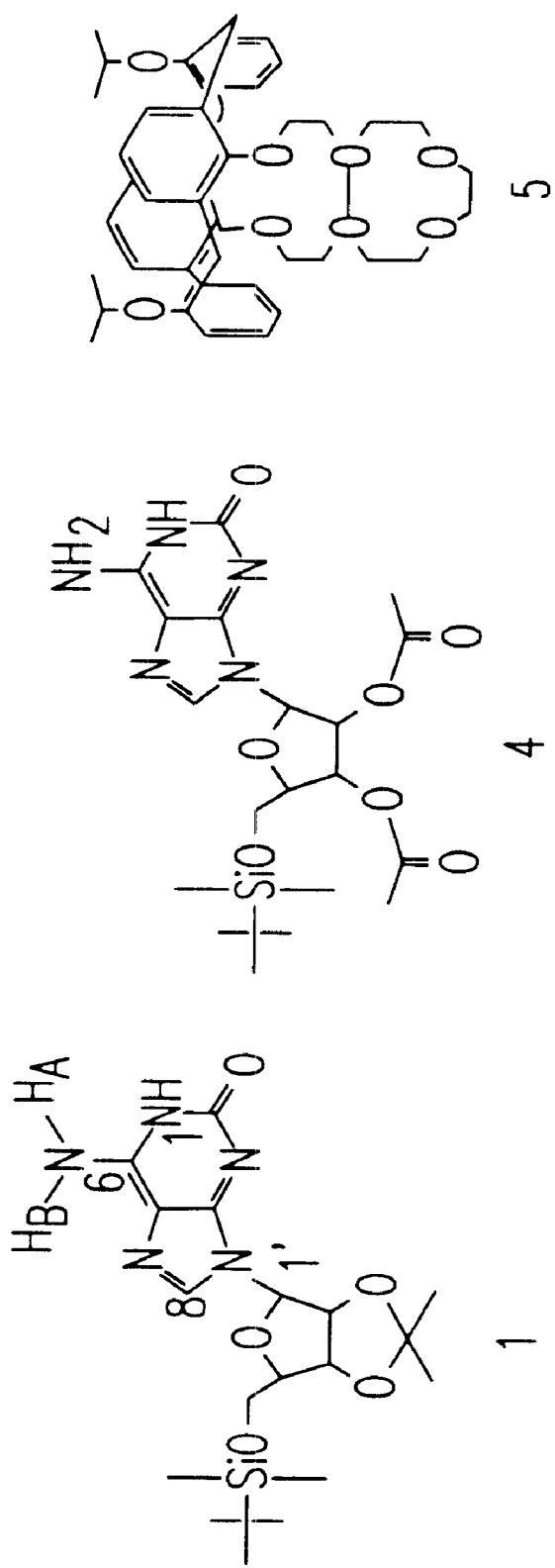
FIG. 5 is a diagram illustrating the structures of 5'-(t-butyl-dimethylsilyl)-2',3'-O-isopropylidene-isoguanosine (isoG 1), 2',3'-Di-O-acetyl-5'-(t-butyl-dimethylsilyl)-isoguanosine (isoG 4), and 1,3-diisopropylcalix[4]arenecrown-6 5.

The self-association and Cs$^+$/K$^+$ binding properties of isopropylidene 1 and 2',3'-O-diacetyl isoG 4 were compared (isoG 1 binds K$^+$ over Na$^+$ by at least 10-fold) (see FIG. 5). The different propensity for 1 and 4 to self-associate in organic solvents was apparent when comparing $^1$H NMR spectra. In the absence of metal ion, isopropylidene 1 forms a hydrogen bonded tetramer 2 in CD$_3$CN (Ka=10$^9$ M$^{-3}$),[17a] while diacetate 4 is monomeric under identical conditions. These results are consistent with the proposal that nucleobase-sugar hydrogen bonds drive the self-association of isopropylidene 1.

Both isopropylidene 1 and diacetate 4 coordinate K$^+$ and Cs$^+$ strongly in CDCl$_3$ and CD$_3$CN. Integration of $^1$H NMR and UV-VIS spectra after metal picrate extraction from water into CDCl$_3$ indicate that 1 and 4 bind K$^+$ and Cs$^+$ to form (isoG)$_8$-M$^+$ 3 (metal picrate titrations also showed that isoG 1 and 4 form octanes, (isoG)-M$^+$ 3 in CD$_3$CN). Since both cesium and potassium picrate are insoluble in CDCl$_3$, spectroscopic measurement of the picrate anion is indirect evidence for cation binding by 1 and 4. Cesium-133 NMR directly showed that these isoG analogs bind Cs$^+$.[19] Distinct $^{133}$Cs NMR spectra were obtained after cesium picrate extraction by isopropylidene 1 (σ −55.2 ppm) and by diacetate 4 (σ −28.4 ppm) (the $^{133}$CS chemical shifts are relative to 0.5 M CsI in D$_2$O at 0° C.). The unique $^{133}$Cs chemical shifts indicate that the electronic environment around Cs$^+$ is different in the two (isoG)$_8$-Cs$^+$ species.

Cation binding was also indicated by a decrease in the $^{133}$Cs T$_1$ value in the presence of isopropylidene 1. Typically, $^{133}$Cs T$_1$ values decrease upon complexation by ionophores, since $^{133}$Cs relaxation is dominated by its nuclear quadrupole and by its reorientational correlation time, t$_c$.[20,21] First, coordination and desolvation change the electric field gradient near Cs$^+$. Second, t$_c$ for an ionophore-metal complex is larger than that for a solvated Cs$^+$. The $^{133}$Cs T$_1$ values in CD$_3$CN were 3.25 s for cesium picrate and 0.0023 s for (isoG 1)$_8$-Cs$^+$. This 1400-fold decrease in $^{133}$Cs T, is then consistent with Cs$^+$ coordination by (isoG 1)$_8$.

Cesium binding constants (K$_a$) for 1 and 4 in CDCl$_3$ were determined from NMR competition experiments with 1,3-diisopropylcalix[4]arenecrown-6 5. Calixarene 5 is a Cs$^+$ selective ionophore, with log K$_a$ (Cs$^+$)=8.8 in CDCl$_3$ (Table 1).[13a] Coordination of Cs$^+$ by calixarene 5 can be monitored by both $^1$H and $^{133}$Cs NMR, since the free and Cs$^+$ bound calixarene 5 are in slow exchange. Addition of one equivalent of calixarene 5 to a CDCl$_3$ solution of (isog 4)$_8$-Cs$^+$ gave two separate $^{133}$Cs NMR signals in a 1.0:1.0 ratio, with one resonance for (isoG 4)$_8$-Cs$^+$ at −28.6 ppm, and one for Cs$^+$-bound calixarene 5 at −61.4 ppm. The diacetate octamer, (isoG 4)$_8$, with a Cs$^+$ binding constant equal to that of calixarene 5, is a potent ionophore (Table 1). Competition experiments showed that isopropylidene 1 binds Cs$^+$ even more strongly than does calixarene 5. Upon addition of ten equivalents of calixarene 5 to a CDCl3 solution containing (isoG 1)$_8$-Cs$^+$ there were no changes in the $^1$H and $^{133}$Cs NMR spectra. This experiment establishes a lower limit of log K$_a$ (Cs$^+$)=9.8 for isopropylidene 1. Calixarene 5 did not remove Cs$^+$ from the isopropylidene octamer, (isoG 1)$_8$-Cs$^+$, as it did in competition experiments with diacetate (isoG 4)$_8$-Cs$^+$. The Cs$^+$ binding constant for isopropylidene 1 is clearly greater than that for diacetate 4, indicating that isoG's sugar group influences the ionophore-cation interaction.

Binding affinity is only one measure of an ionophore's utility. An effective ionophore should also be ion selective. $^1$H NMR spectroscopy was used to determine the Cs$^+$/K$^+$ binding selectivities for diacetate 4 and isopropylidene 1. Since (isoG)$_8$-K$^+$ and (isoG)$_8$-Cs$^+$ were in slow exchange on the NMR time-scale for both 1 and 4, Cs$^+$/K$^+$ selectivities could be determined by integrating NMR signals for the separate (isoG)-M$^+$ species. Diacetate 4 had little Cs$^+$/K$^+$ selectivity. Extraction of water containing equimolar concentrations (4.5 mM) of potassium picrate and cesium picrate with a CDCl$_3$ solution of diacetate 4 (16 mM) gave 53% (isoG 4)-K$^+$ and 47% (isoG 4)$_8$-Cs$^+$, for a Cs$^+$/K$^+$ selectivity of 0.89. The free energy difference for coordination of Cs$^+$ vs K$^+$ in CDCl$_3$ by 4 is small ($\Delta\Delta$G<0.05 kcal/mol) (a similar Cs$^+$/K$^+$ selectivity factor of 0.83 (($\Delta\Delta$G=0.11 kcal/mol) in CD$_3$CN was determined from titration of (isoG 4)$_8$-Cs$^+$ with potassium picrate).

Figure 6:
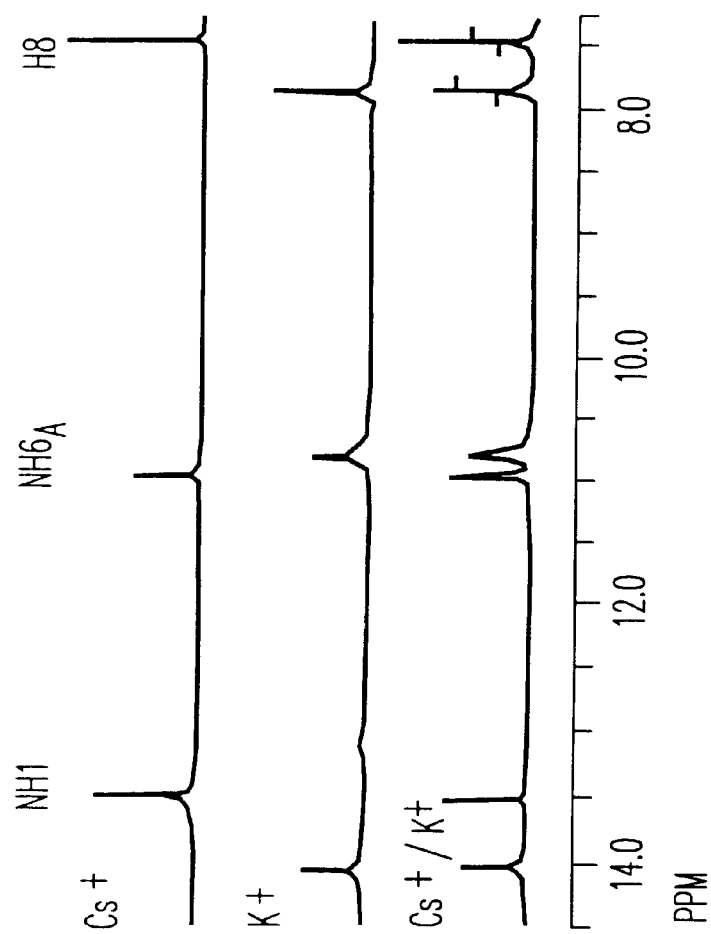
FIG. 6 illustrates a region of the 500 MHZ $^1$H NMR spectra of a CDCl$_3$ solution of (isoG 1)$_8$-M$^+$ 3 (2.0 mM) at 25° C. The top spectrum is of a sample formed by extraction of KI (2.5 M) from water. The middle spectrum is of a sample formed by extraction of CsI (0.005 M) from water. The bottom spectrum shows a sample after extraction from water containing KI (2.5 M) and CsI (0.005 M).

In contrast to the indiscriminate diacetate 4, isopropylidene 1 is a Cs$^+$ selective ionophore. When a CDCl$_3$ solution of isopropylidene 1 was stirred with water containing equimolar potassium picrate and cesium picrate, only Cs$^+$ was extracted into the organic phase. To observe any (isoG 1)8-K$^+$ complex, the K$^+$/Cs$^+$ ratio had to be increased. Extraction of water containing 2.50 M KI and 0.005 M CsI with a CDCl$_3$ solution of 1 gave (isoG 1)$_8$-K$^+$ ($\sigma$ 14.03 for NH1) and (isoG 1)$_8$-Cs$^+$ ($\sigma$ 13.53 for NH1) in a 1.5:1 ratio (FIG. 6). Thus, isopropylidene 1 has a Cs$^+$/K$^+$ binding selectivity of approximately 333/1, corresponding to a relative free energy that is 3.5 kcal/mol more favorable for Cs$^+$ binding (see Table 1).

TABLE 1

Cs$^+$Binding Constants and Cs$^+$/K$^+$Selectivities for Various Ionophores.

| Ionophore | log K$_a$ (Cs$^+$) | K$_a$ (Cs$^+$)/K$_a$ (K$^+$) | Ref. |
|---|---|---|---|
| Calix[4]crown 5 | 8.8 | 250 | 13a[a] |
| (IsoG 4)$_8$ | 8.8 | 0.86 | this application[b] |
| (IsoG 1)$_8$ | >9.8 | 333 | this application |

[a]In CHCl$_3$ saturated with H$_2$O at 22° C.
[b]In CDCl$_3$ saturated with H$_2$O at 20° C.

Thus, it has been shown that isoG's sugar substituents influences the self-assembled ionophore's cation selectivity. Compared with diacetate 4, both the absolute Cs$^+$ binding constant and the Cs$^+$/K$^+$ selectivity are significantly greater for isopropylidene 1. This change in the ribose's 2',3'-substitution alters the Cs$^+$/K$^+$ selectivity ratio by 400-fold. Isopropylidene 1 likely forms such an effective self-assembled ionophore due to "preorganization" on two different levels.[20] First, the 2',3'-isopropylidene constrains the sugar conformation so as to optimize hydrogen bonds that stabilize the tetramer, (isoG 1)$_4$. Once self-assembled, the tetramer's four carbonyl oxygens are then well oriented to coordinate cations.[11b] From a practical viewpoint, self-association of isopropylidene 1 demonstrates the ability to bind metal cations with high affinity and selectivity.

EXPERIMENTAL SECTION

Synthesis.

Isopropylidene 1 was prepared as described.[1] Isopropylidene 1 was purified by flash chromatography on silica gel using 10:1 CH$_2$Cl$_2$:EtOH as eluant. N$^6$-Formamidine isoG (a in FIG. 7) was synthesized as described.[25]

Figure 7:
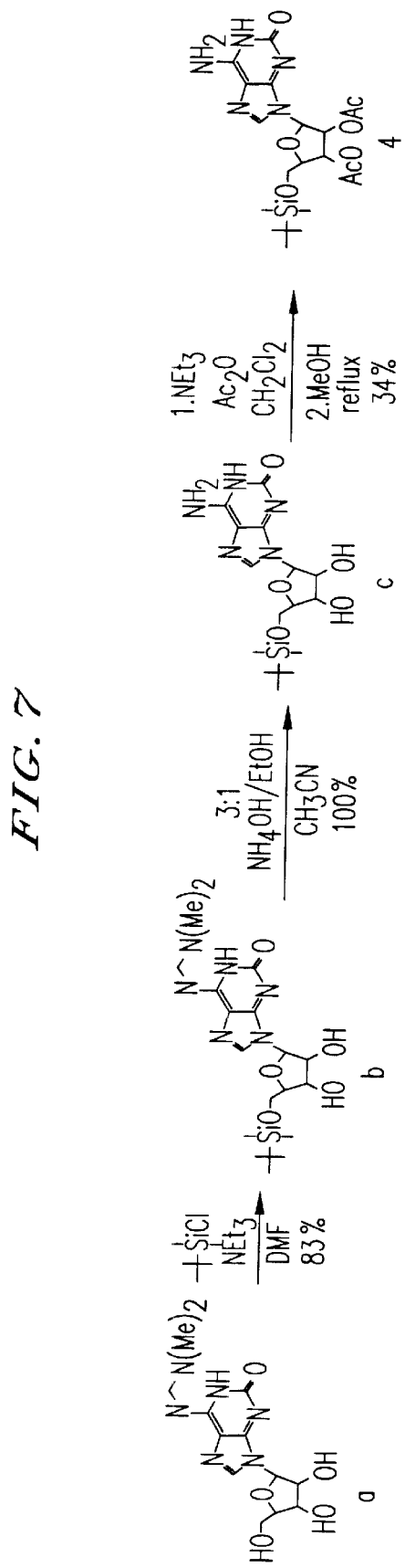
FIG. 7 is a diagram illustrating the synthesis of 2',3'-Di-O-acetyl-5'-(t-butyl-dimethylsilyl)-isoguanosine (isoG 4).
Figure 8:
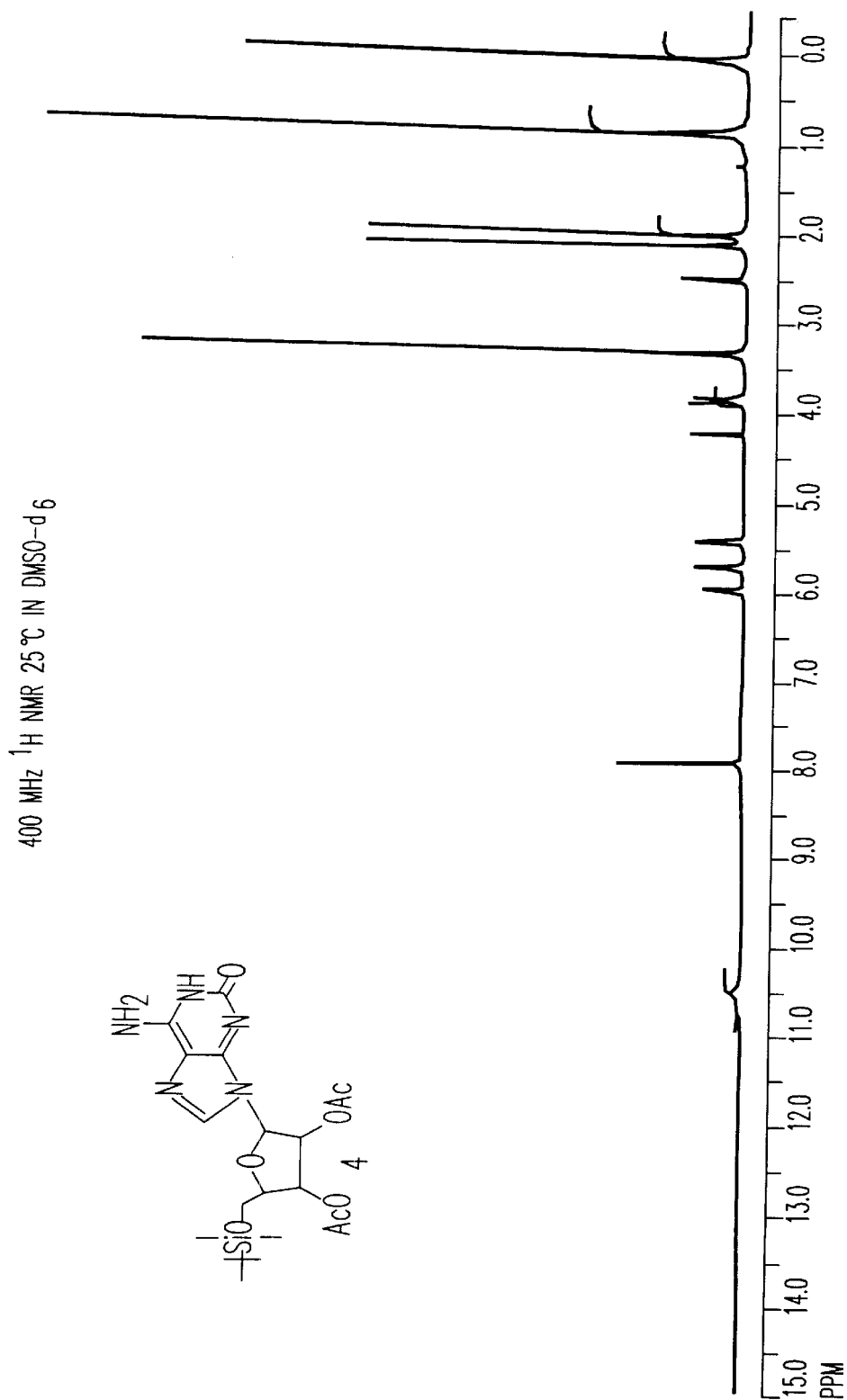
FIG. 8 illustrates a 500 MHz $^1$H NMR spectrum of 2',3'-Di-O-acetyl-5'-(t-butyl-dimethylsilyl)-isoguanosine (isoG 4) (40 mM) in d$_6$-DMSO at 25° C. This spectrum indicates that isoG 4 is monomeric in d$_6$-DMSO.
Figure 10C:
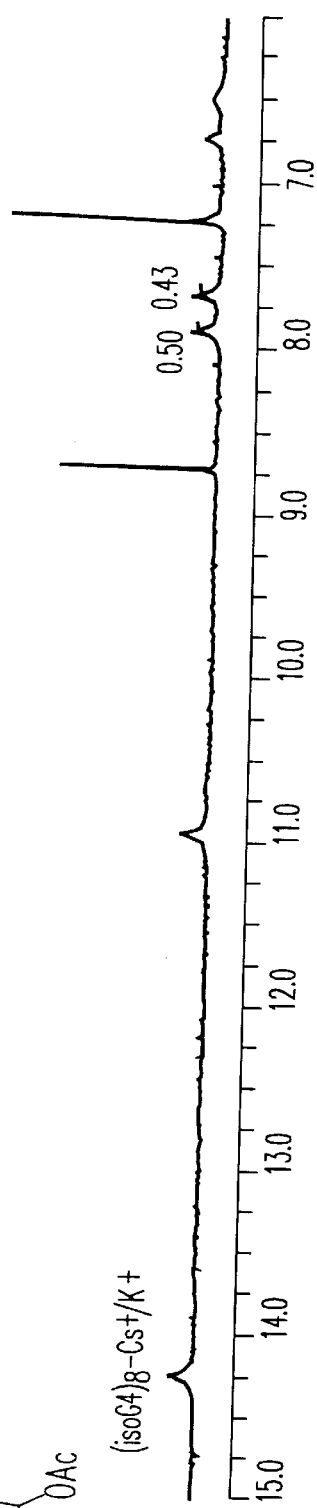
FIG. 10 illustrates a region of the 500 MHz $^1$H NMR spectrum of 2',3'-Di-O-acetyl-5'-(t-butyl-dimethylsilyl)-isoguanosine (isoG 4) (16 mM) in CDCl$_3$ at 0° C. A) After extraction with water containing 4.5 mM cesium picrate; B) After extraction with water containing 4.5 mM potassium picrate; C) After extraction with water containing 4.5 mM potassium picrate and 4.5 mM cesium picrate. Integration of the diacetate's H8 resonance indicates a 57:43 ratio of (isoG 4)$_8$-K$^+$ to (isoG 4)$_8$-Cs$^+$.
Figure 11A:
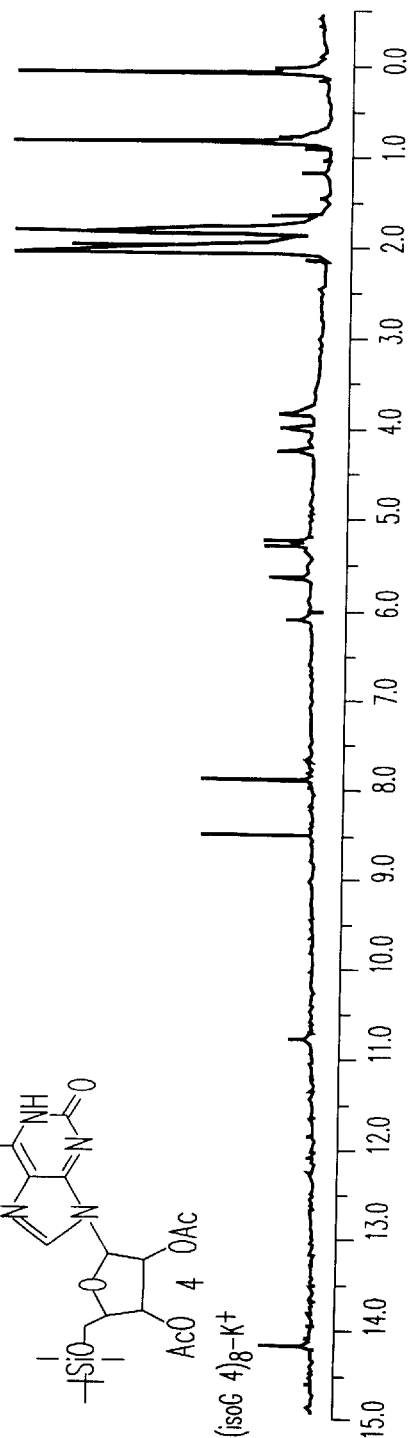
FIG. 11 illustrates a 400 MHz $^1$H NMR spectrum of 2',3'-Di-O-acetyl-5'-(t-butyl-dimethylsilyl)-isoguanosine (isoG 4) (2.0 mM) in CD$_3$CN at 25° C. A) After titration with 0.50 mM (2 eq. per octamer) potassium picrate; B) After titration with-0.50 mM (2 eq. per octamer) cesium picrate; C) IsoG 4 (2.5 mM) with 0.31 mM (1 eq. per octamer) potassium picrate and 0.31 mM cesium picrate (1 eq. per octamer). The two sets of separate resonances for (isoG 4)$_8$K$^+$ and (isoG 4)$_8$-Cs$^+$ show there is little Cs$^+$/K$^+$ selectivity for isoG 4.
Figure 11B:
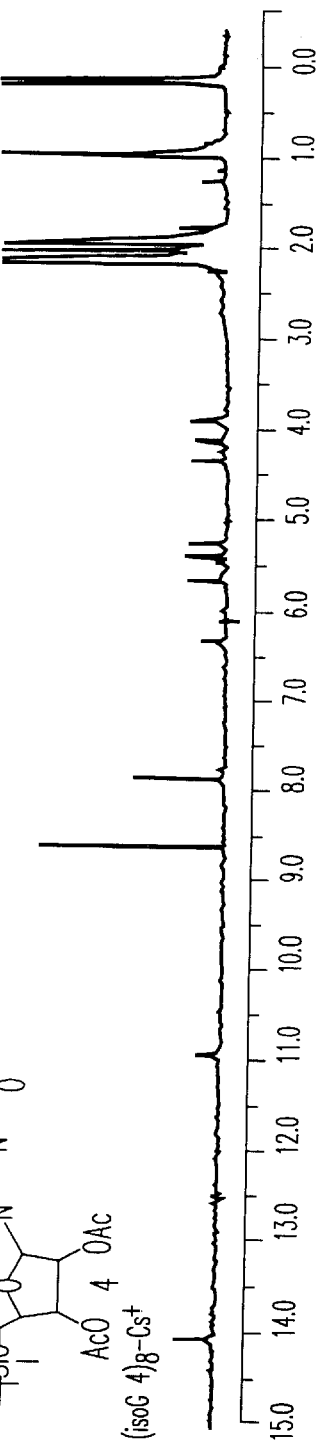
Figure 11C:
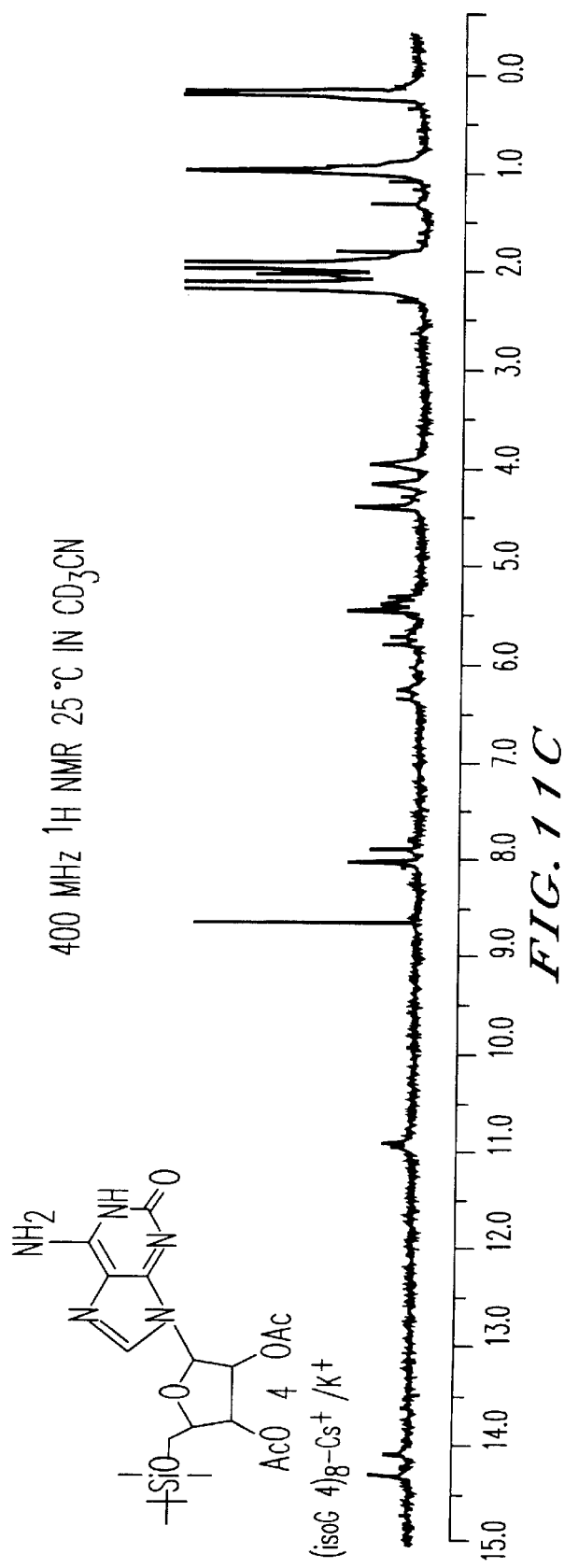
Figure 12:
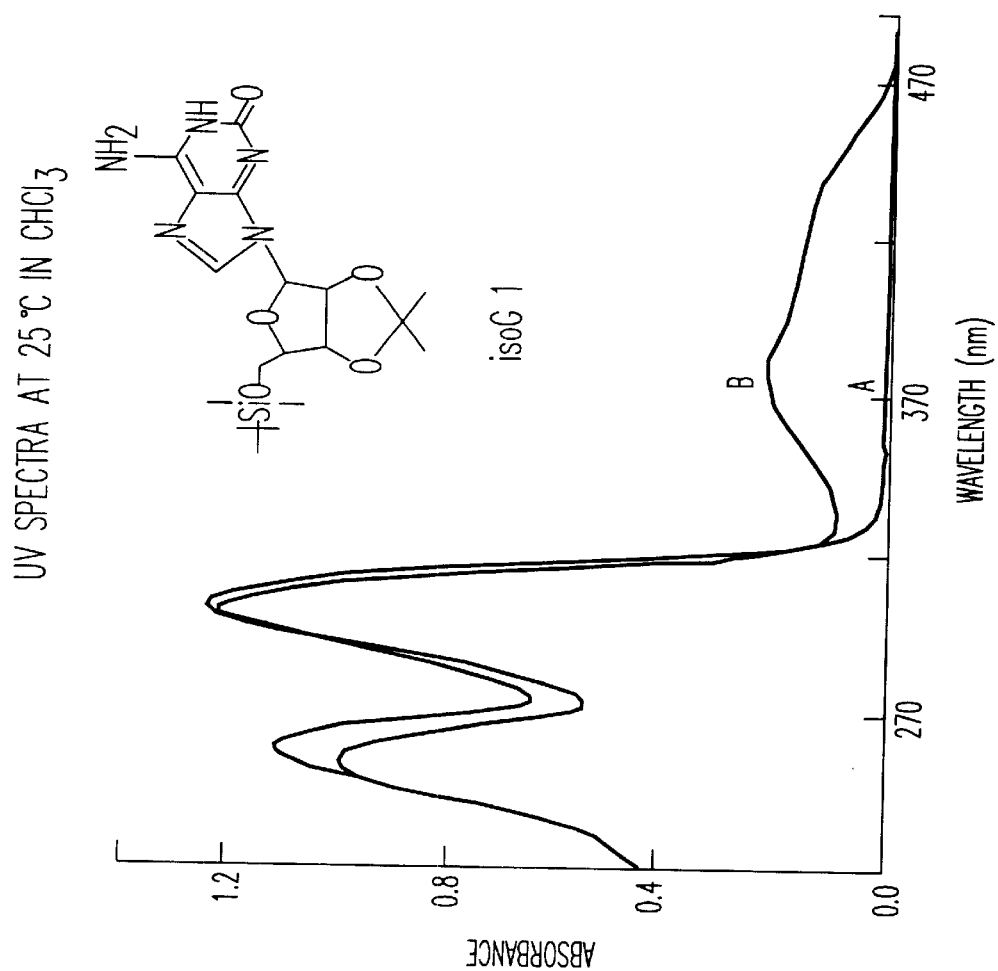
FIG. 12 illustrates an optical spectra of a CHCl$_3$ solution of 5'-(t-butyl-dimethylsilyl)-2',3'-O-isopropylidene-isoguanosine (isoG 1) (0.11 mM) at 25° C.; A) Before cesium picrate extraction; B) After extraction of an aqueous cesium picrate (3.0 mM) solution. Integration of the isoG 1 absorption at 295 nm and the picrate absorption at 378 nm indicates formation of (isoG 1)$_8$-Cs$^+$.
Figure 15C:
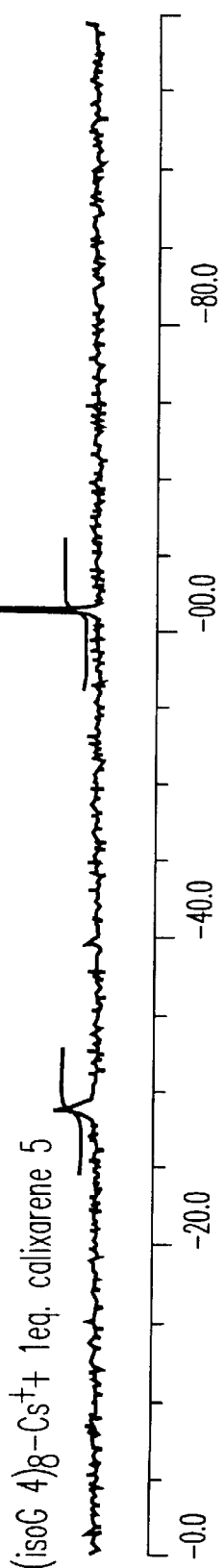
FIG. 15 illustrates a 65.6 MHz $^{133}$Cs NMR spectra in CDCl$_3$ at 0° C.; A) For (isoG 4)$_8$-Cs$^+$ (2.0 mM); B) For calixarene 5 (2.0 mM); C) for a 1:1 mixture of (isoG 4)$_8$-Cs$^+$ and calixarene 5 (both 2.0 mM). Integration of the two signals gives a 1:1 ratio. This experiment shows that (isoG 4)$_8$ and calixarene 5 have similar Cs$^+$ association constants.

5'-(tert-Butyldimethylsilyl)-N$^6$-formamidine isoG (b in FIG. 7).

To a solution of N$^6$-formamidine isoG a (0.52 g, 1.53 mmol) in DMF (15 mL) was added NEt$_3$ (0.61 g. 0.84 mL, 6.03 mmol) and TBDMS-Cl (0.88 g, 5.85 mmol). The reaction mixture was stirred at rt for 48 h, diluted with CH$_2$Cl$_2$ (30 mL) and the organic layer was washed with H$_2$O (15 mL), 0.01 N HCl (15 mL), saturated NaHCO$_3$ (15 mL), and saturated NaCl (15 mL). The organic layer was dried over Na$_2$SO$_4$ and concentrated in vacuo to give a yellow gum. The crude product was triturated with diethyl ether to give b (0.57 g, 83 %) as a white solid. R$_f$0.75 (CH$_2$Cl$_2$/MeOH, 3:2). UV (MeOH), $\lambda$max ($\epsilon$ 227 (24000), 260 (14000), 345 (25000). $^1$H NMR (400 MHz, DMSO-d$_6$) $\delta$ 0.04 (s, 6 H), 0.86 (s, 9 H0, 3.09 (s, 3 H), 3.19 (s, 3 H), 3.71 (dd, J=4.4, 11.3 Hz, 1 H), 3.81 (dd, J=3.8, 11.3 Hz, 1 H), 3.89 (ddd, J=3.8, 4.1, 4.4 Hz, 1 H), 4.07 (ddd, J=4.1, 5.0, 5.4 Hz, 1 H), 4.38 (ddd, J=5.0, 5.2, 5.9 Hz, 1 H), 5.18 (d, J=5.4 Hz, 1 H), 5.51 (d, J=5.9 Hz, 1 H), 5.69 (d, J=5.2 Hz, 1 H), 7.97 (s, 1 H), 9.11 (s, 1 H), 11.05 (br s, 1 H). $^{13}$C NMR (50 MHz, DMSO-d$_6$) $\delta$ –5.5, 18.0, 25.8, 34.3, 63.0, 69.9, 73.2, 84.3, 86.3, 113.1, 139.3, 154.4, 156.4, 157.7, 161.0. LRMS (FAB), m/z (rel int) 73 (100), 207 (88), 453 ([M+1]$^+$, 33). HRMS (FAB), calc. For C$_{19}$H$_{33}$N$_6$O$_5$Si 453.2282, found 453.2285.

5'-(tert-Butyldimethylsilyl)-isoguanosine (c in FIG. 7).

To a solution of 5'-(tert-butyldimethylsilyl)-N$^6$-formamidine isoG b (0.30 g, 0.66 mmol) in CH$_3$CN (2 mL) was added EtOH (2 mL) and NH$_4$OH (6 mL). The reaction mixture was stirred at rt for 16 h after which time TLC indicated the reaction was complete. The solvent was evaporated to give c (0.26 g, 100%) as a white solid. This material was used without further purification in the next step. R$_f$0.58 (CH$_2$Cl$_2$/MeOH, 3:2). $^1$H NMR (200 MHz, DMSO-d$_6$) $\delta$ 0.05 (s, 6 H), 0.87 (s, 9 H), 3.66–3.90 (m, 3 H), 4.08 (m, 1 H), 4.31 (dd, J=4.7, 4.7 Hz, 1 H), 5.14 (br s, 1 H), 5.22 (br s, 1 H), 5.66 (d, J=4.7 Hz, 1 H), 7.46 (br s, 1 H), 7.90 (s, 1 H). LRMS (FAB), m/z (rel int) 73 (100), 75 (27), 152 (69), 398 ([M+1]$^{+,18}$). HRMS (FAB), calc. For C$_{16}$H$_{28}$N$_5$O$_5$Si 398.1860, found 398.1842.

2',3'-Di-O-acetyl-5'-(tert-Butyldimethylsilyl)-isoguanosine (4 in FIG. 7).

To a suspension of 5'-(tert-butyldimethylsilyl)-isoG c (0.26 g, 0.66 mmol) in CH$_2$Cl$_2$ was added NEt$_3$ (0.67 g, 0.93 mL, 6.63 mmol) and acetic anhydride (0.68 g, 0.63 mL, 6.63 mmol). The reaction was allowed to stir at rt for 19 h after which time TLC indicated that the reaction was complete. The reaction was diluted with CH$_2$Cl$_2$ (25 mL) and the organic layer was washed with 0.01 N HCl (25 mL), sat NaHCO$_3$ (25 mL), and sat NaCl (25 mL). The organic layer was dried over Na$_2$SO$_4$ and concentrated in vacuo to give a yellow oil. The $^1$H NMR of the crude product showed many acetate signals. Thus, MeOH (10 mL) and CH$_2$Cl$_2$ (5 mL) were added and the reaction mixture was refluxed for 72 h. After this time the two spots with R$_f$0.69 and 0.53 (CH$_2$Cl$_2$/MeOH, 10: 1) were converted to two lower running spots of R$_f$0.41 and 0.27 (major). This mixture was purified by silica gel chromatography to give 2',3'-di-O-acetyl-5'-(tert-butyldimethylsilyl)-isoG 4 (0.11 g, 34%) as a white solid. R$_f$0.27 (CH$_2$Cl$_2$/MeOH, 10:1). UV (MeOH), $\lambda$max ($\epsilon$) 215 (32000), 252 (12000), 295 (12000). $^1$H NMR (400 MHz, DMSO-$d_6$) δ 0.07 (s, 6 H), 0.88 (s, 9 H), 2.00 (s, 3 H), 2.11 (s, 3 H), 3.81 (dd, J=3.5, 11.3 Hz, 1 H), 3.88 (dd, J=3.5, 11.3 Hz, 1 H), 4.20 (m, 1 H), 5.41 (dd, J=2.9, 5.2 Hz, 1 H), 5.70 (dd, J=5.2, 6.6 Hz, 1 H), 5.96 (d, J=6.6 Hz, 1 H), 7.62 (br s, 1 H), 7.91 (s, 1 H), 10.51 (br s, 1 H). $^{13}$C NMR (50 MHz, CDCl$_3$) δ −5.5, 18.4, 20.4, 20.7, 25.9, 63.1, 71.8, 74.2, 83.7, 83.7, 110.0, 136.5, 151.5, 154.5, 158.0, 169.4, 170.0. LRMS (FAB), m/z (rel int) 66 (29), 73 (100), 152 (40), 482 ([M+1]$^+$, 38). HRMS (FAB), cailc. for C$_{20}$H$_{32}$N$_5$O$_7$Si 482.2071, found 482.2056.

Preparation of Potassium and Cesium Picrate:

Potassium picrate was prepared by neutralizing picric acid with an equal molar amount of potassium or cesium hydroxide in EtOH. Solid impurities were removed by filtration. The resulting metal picrate salts, which precipitated from solution, were recrystallized twice from water and dried in a vacuum desiccator for 2 days. The recrystallized metal picrates salts were characterized by $^1$H NMR, UV spectroscopy, and elemental analysis.

NMR Experiments

Most NMR experiments were performed on a Bruker AMX-500 NMR spectrometer. The spectrometer $^1$H frequency was 500.13 MHz and its $^{133}$Cs frequency was 65.6 MHz. The temperature was controlled to ±0.1° C. The spectral window was 20 ppm for $^1$H and 300 ppm for $^{133}$Cs. Typical 90° pulse widths were 11 μs for $^1$H and 7.4 μs for $^{133}$Cs. The 133Cs chemical shifts were referenced relative to 0.5 M CsI in D$_2$O at 0° C.

Metal Cation Picrate Extractions:

To a glass vial containing 1 mL of a 16 mM solution of isoG 1 or 4 in CDCl$_3$ was added 1 mL of a 4.5 mM solution of metal picrate in distilled water. This CDCl$_3$/H$_2$O mixture was stirred for 1 h at rt. The mixture was then transferred to an eppendorf tube and centrifuged for 5 min to force the organic layer to the bottom of the tube. An aliquot (0.5 mL) of the CDCl$_3$ layer was carefully removed with a syringe and transferred to an NMR tube for measurement. The 500 MHz $^1$H NMR spectrum of the sample was recorded at 0° C. The stoichiometry for (isoG)$_8$-M$^+$ was determined by comparing the integration of the picrate's $^1$H resonance at 8.66 ppm with the integration of the isoG resonances.

Competition Experiment for Potassium Picrate and Cesium Picrate Extraction.

To a glass vial containing 1 mL of a 16 mM solution of isoG 4 in CDCl$_3$ was added a 1 mL solution of 4.5 mM potassium picrate and 4.5 mM cesium picrate in H$_2$O. This CDCl$_3$/H$_2$O mixture was stirred for 1 h at rt. The mixture was then transferred to an eppendorf tube and centrifuged for 5 min to force the organic layer to the bottom of the tube. An aliquot (0.5 mL) of the CDCl$_3$ layer was carefully removed with a syringe and transferred to an NMR tube for measurement. The $^1$H NMR (500 MHz) spectrum was recorded at 0° C. The relative amounts of (isoG)$_8$-K$^+$ and (isoG)$_8$-Cs$^+$ were determined by comparing the integration of the H8 resonance of (isoG)$_8$-K$^+$ at 7.89 ppm, with the integration of the H8 resonance of (isoG)$_8$-Cs$^+$ at 7.68 ppm.

Metal Picrate Titrations.

A series of NMR tubes containing a solution of isoG 4 (2.6 mM) in CD$_3$CN, and metal cation picrate in CD$_3$CN in increasing increments (0.02 mM, 0.04 mM, 0.08 mM, 0.16 mM, 0.32 mM) were vortexed for 2 min. The 400 MHz $^1$H NMR spectra were recorded at 25° C. The stoichiometry of the isoG-metal complex was determined by comparing the integration of the picrate's $^1$H resonance at 8.66 ppm with the integration of the isoG resonances.

$^{133}$Cs T$_1$ Determination:

The inversion-recovery method was used to determine the $^{133}$Cs spin lattice relaxation time, T$_1$ for cesium picrate (10 mM) and (isoG 1)$_8$-Cs$^+$ picrate (8 mM) in CD$_3$CN at 25° C. The T$_1$ values were estimated by a null point determination method in a single inversion recovery experiment. Incremental values for τ of 0.05 sec and 0.002 sec were used for cesium picrate and (isoG 1)$_8$-Cs$^+$ picrate, respectively, to determine the null point. Selected acquisition parameters of the individual spectra were as follows: spectral window, 200 ppm; relaxation delay 10 S; $^{133}$Cs 90 degree pulse 7.3 us; number of scans 300.

Competition of (isoG 4)$_8$-Cs$^+$ with Calixarene 5.

To a glass vial containing 1 mL of a 16 mM solution of isoG 4 in CDCl$_3$ was added 1 mL of a 4.5 mM solution of cesium picrate in distilled water. This CDCl$_3$/H$_2$O mixture was stirred for 1 h at rt. The mixture was then transferred to an eppendorf tube and centrifuged for 5 min to force the organic layer to the bottom of the tube. An aliquot (0.5 mL) of the CDCl$_3$ layer was carefully removed with a syringe and transferred to an NMR tube for measurement. To this was added 50 mL of a 20 mM solution of calixarene 5, so that the overall solution was 1.8 mM4 (isoG 4)$_8$-Cs$^+$ and 1.8 mM calixarene 5. The $^1$H NMR (500 MHz) and $^{133}$Cs NMR (65.6 MHz) spectra were recorded at 0° C. The relative amounts of (isoG 4)$_8$-Cs$^+$ and (isoG 4)$_4$ were determined by comparing the integration of $^{133}$Cs resonance for (isoG)$_8$-Cs$^+$ at −28.4 ppm with the integration of the calixarene-Cs$^+$ resonance at −61.4 ppm.

Competition of (isoG 1)$_8$-Cs$^+$ with Calixarene 5.

To a glass vial contain 1 mL of a 16 mM solution of isoG 1 in CDCl$_3$ was added 1 mL of a 4.5 mM solution of cesium picrate in distilled water. This CDCl$_3$/H$_2$O mixture was stirred for 1 h at rt. The mixture was then transferred to an eppendorf tube and centrifuged for 5 min to force the organic layer to the bottom of the tube. An aliquot (0.5 mL) of the CDCl$_3$ layer was carefully removed with a syringe and transferred to an NMR tube for measurement. To this was added varying amounts of a 20 mM solution of calixarene 5, so that the overall solution was 1.7 mM (isoG 1)$_8$-Cs$^+$ and between 1.7–17 mM in calixarene 5. The $^1$H NMR (500 MHz) and $^{133}$Cs NMR (65.6 MHz) spectra-were recorded at 0° C.

Determination of Cs$^+$/K$^+$ Specificity for Isopropylidene isoG 1.

Because of solubility problems in obtaining high concentrations of potassium picrate, the more soluble iodide salts were used to determine the Cs$^+$/K$^+$ specificity for isopropylidene 1. To a glass vial containing 1 mL of a 16 mM solution of isoG 1 in CDCl$_3$ was added a 1 mL solution of 2.5 M KI and 0.005 M CsI in H$_2$O. This CDCl$_3$/H$_2$O mixture was stirred for 1 h at rt. The mixture was then transferred to an eppendorf tube and centrifuiged for 5 min to force the organic layer to the bottom of the tube. An aliquot (0.5 nL) of the CDCl$_3$ layer was carefully removed with a syringe and transferred to an NMR tube for measurement. The $^1$H NMR (500 MHz) spectrum was recorded at 25° C. The Cs$^+$/K$^+$ specificity was determined by peak integration of the separate K$^+$ and Cs$^+$-bound species.

TABLE 2

$^1$H NMR chemical shifts (ppm) for isoG diacetate 4.

| Resonance | DMSO-$d_b{}^a$ | $CDCl_a{}^b$ | $CDCl_a$+K30 $^c$ | $CDCl_a$+Cs30 $^d$ | $CD_aCN$+K30 $^e$ | $CD_aCN$+Cs30 $^f$ |
|---|---|---|---|---|---|---|
| NH1 | 10.51 | | 14.21 | 14.24 | 14.24 | 14.02 |
| NH6$_A$ | 7.62 | | 10.95 | 10.95 | 10.84 | 10.90 |
| NH6$_B$ | 7.62 | | 6.53 | 6.74 | 6.19 | 6.31 |
| H8 | 7.91 | 7.86 | 7.89 | 7.68 | 7.98 | 7.84 |
| H1$^1$ | 5.96 | 6.14 | 5.74 | 5.86 | 5.73 | 5.63 |
| H2$^1$ | 5.70 | 5.55 | 5.40 | 5.38 | 5.38 | 5.37 |
| H3$^1$ | 5.41 | 5.42 | 5.40 | 5.38 | 5.33 | 5.24 |
| H4$^1$ | 4.20 | 4.25 | 4.33 | 4.37 | 4.33 | 4.33 |
| H5$^f$ | 3.88 | 3.90 | 4.01 | 4.04 | 4.09 | 4.11 |
| H5$^f$ | 3.81 | 3.86 | 3.88 | 3.93 | 3.91 | 3.88 |
| CH$_1$ A | 211 | 2.15 | 2.15 | 2.17 | 2.15 | 2.11 |
| CH$_1$ B | 2.00 | 2.02 | 2.01 | 24 | 2.08 | 2.02 |
| tBu | 0.88 | 0.93 | 0.93 | 0.94 | 0.95 | 0.94 |
| SiMe A | 0.07 | 0.14 | 0.15 | 0.10 | 0.18 | 0.17 |
| SiMe B | 0.07 | 0.14 | 0.15 | 0.16 | 0.15 | 0.14 |

$^a$400 MHz at 25° C.
$^b$500 MHz at 20° C.
$^c$500 MHz at 0° C. after extraction of potassium picrate.
$^d$500 MHz at 0° C. after extraction of cesium picrate.
$^e$400 MHz at 25° C. with excess potassium picrate.
$^f$400 MHz at 25° C. with excess cesium picrate.

TABLE 3

$^{133}$Cs NMR chemical shifts$^a$

| Species | α(ppm) |
|---|---|
| (IsoG 1)$_8$-Cs$^+$ | −28.6 |
| (IsoG 4)$_8$-Cs$^+$ | −55.1 |
| calixarene 5-Cs$^+$ | −61.4 |

$^a$At 65.6 MHz in CDCl$_3$ at 0° C. Relative to KI in D$_2$O at 0° C.

REFERENCES

The following publications are hereby incorporated by reference.

1. "Self-Assembled Ionophores from Isoguanosine." Davis, J. T.; Tirumala, S.; Jenssen, J. R.; Radler, E.; Fabris, D., *J. Org. Chem.* 1995, 60, 4167–4176.
2. "Self-Assembled Ionophores. An Isoguanosine-K+ Octamer." Tirumala, S.; Davis, J. T., *J. Am. Chem. Soc.* 1997, accepted with revisions.
3. "The Role of Ribose Conformation in Cesium Selective Self-Assembled Ionophores from Isoguanosine." Tirumala, S.; Marlow, A. L.; Davis, J. T., submitted for publication in *J. Am. Chem. Soc.* 1997.
4. "Solid Phase Extraction of Ions Using Molecular Recognition Technology." Izatt, R. M.; Bradshaw, J. S.; Bruening, R. L.; Tarbet, B. J.; Bruening, M. L., *Pure & Appl. Chem.* 1995, 67, 1069–1074.
5. "Solvent Extraction Recovery of Byproduct $^{137}$Cs and $^{90}$Sr from HNO$_3$ Solutions-A Technology Review and Assessment." Schultz, W. W.; Bray, L. A., *Sep. Sci. Tech.* 1987, 22, 191–214.
6. (a) "Equilibrium Aspects of the Extraction of Cesium Nitrate by Dicyclohexano-21-crown-7, Dibenzo-21-crown-7 and bis-[tert-Alkylbenzo]-21-crown-7 in 1.2-Dichloro-berzene." Deng, Y.; Sachlben, R. A.; Moyer, B. A., *J. Chem. Soc. Faraday Trans.* 1995, 91, 4215–4222. (b) "Selective Extraction of Cesium from Acidic Nitrate Solutions with Didodecylnapthalenesulfonic Acid Synergized with Bis(tert-butylbenzo)-21-crown-7." McDowell, W. J.; Case, G. N.; McDonough, J. A.; Bartsch, R. A., *Anal. Chem.* 1992, 64, 3013–3017.
7. "Synthesis, Complexation, and Membrane Transport Studies of 1,3-Alternate Calix[4]arene-crown-6 Conformers: A New Class of Cesium Selective Ionophores." Casnati, A.; Pochini, A.; Ungaro, R.; Ugozzoli, F.; Arnaud, F.; Fanni, S.; Shwing, M.; Egherink, R. J. M.; De Jong, F.; Reinhoudt, D. N., *J. Am. Chem. Soc.* 1995, 117, 2767–2777.
8. "Molecular Recognition of Necleotides by the Guanidinium Unit at the Surface of Aqueous Micelles and Bilayers. A Comparison of Microscopic and Macroscopic Interfaces." Onda, M.; Yoshiva, K.; Koyano, H.; Ariga, K.; Kunitake, T., *J. Am. Chem. Soc.* 1996, 118, 8524–8530.
9. Environmental Radioactivity; Eisenbud, M., *Academic Press*, London, 1987.
10. (a) Bradshaw, J. S.; Baxter, S. L.; Lamb, J. D.; Izatt, R. M.; Christensen, J. J., *J. Am. Chem. Soc.* 1981, 103, 1821–1827. (b) Baker, D. S.; Gold. V.; Sghibartz, C. M., *J. Chem Soc. Perkin II* 1983, 1121–1132. (c) McDowell, W. J.; Case, G. N.; McDonough, J. A.; Bartsch, R. A., *Anal. Chem.* 1992, 64, 3013–3017. (d) Deng, Y.; Sachleben, R. A.; Moyer, B. A., *A. J. Chem. Soc. Faraday Trans.* 1995, 91, 4215–4222.
11. For examples of Cs$^+$ ionophores, see: (a) Cram, D. J.; Carmack, R. A.; deGrandpre, M. P.; Lein, G. M.; Goldberg, I.; Knobler, C. B.; Maverick, E. F.; Trueblood, K. N., *J. Am. Chem. Soc.* 1987, 109, 7068–7073. (b) Bryant, J. A.; Ho, S. P.; Knobler, C. B.; Cram, D. J.,*J. Am. Chem. Soc.* 1990, 112, 5837–5843. (c) Krakowiak, K.; Bradshaw, J. S.; Zhu, C.; Hathaway, J. K.; Dalley, N. K.; Izatt, R. M., *J. Org. Chem.* 1994, 59, 4082–4086.
12. Ungaro, R.; Casnati, A.; Ugozzli, F.; Pochini, A.; Dozol, J. F.; Hill, C.; Rouquette, H., *Angew. Chem. Int. Ed. Engl.* 1994, 33, 1506–1509.
13. (a) Casnati, A.; Pochini, A.; Ungaro, R.; Ugozzoli, F.; Arnaud; Fanni, S.; Schwiing, M. J.; Egberink, R. J. M.; de Jong, F.; Reinhoudt, D. N., *J. Am. Chem. Soc.* 1995, 117, 2767–2777. (b) Rudkevich, D. M.; Mercer-Chalmers, J. D.; Verboom, W.; Ungaro, R.; de Jong, F.; Reinhoudt, D. N., *J. Am. Chzem. Soc.* 1995, 117, 6124–6125.

14. (a) Nechifor, A. M.; Philipse, A. P.; de Jong, F.; van Duynhoven, J. P. M.; Egberink, R. J. M.; Reinhoudt, D. N., *Langmuir* 1996, 12, 3844–3854. (b) Arnaud-Neu, F.; Asfari, Z.; Souley, B.; Vicens, J., *New J. Chem.* 1996, 20, 453–463.
15. For examples of self-assemblies constructed using hydrogen bonds, see: (a) Lawrence, D. S.; Jiang, T.; Levitt, M., *Chem. Rev.* 1995, 95, 2229–2260. (b) Philp, D.; Stoddart, J. F., *Angew. Chem. Int. Ed. Engl.* 1996, 35, 1154–1196. (c) Zimmerman, S. C.; Duerr, B. F., *J. Org. Chem.* 1992, 57, 2215–2217. (d) Persico, F.; Wuest, J. D., *J. Org. Chem.* 1993, 58, 95–99. (e) Branda, N.; Wyler, R.; Rebek, J., Jr. *Science* 1994, 263, 1267–1268. (f) Yang, J.; Marenda, J. L.; Geib, S. J.; Hamilton, A. D., *Tetrahedron Lett.*, 1994, 35, 3665–3668. (g) Mascal, M.; Hext, N. M.; Warmuth, R.; Moore, M. H.; Turkenburg, J. P., *Angew. Chem. Int. Ed. Engl.* 1996, 35, 2204–2206.
16. For examples of self-assembled ionophores, see: (a) Schepartz, A.; McDevitt. J. P., *J. Am. Chem. Soc.* 1989, 111, 5976–5977. (b) Schall, O. F.; Robinson, K.; Atwood, J. L.; Gokel, G. W., *J. Am. Chem. Soc.* 1993, 115, 5962–5969. (c) Gottarelli, G.; Masiero, S.; Spada, G. P, *J. Chem. Soc. Chem. Commun.* 1995, 2555–2557.
17. (a) Davis, J. T.; Tiiumala, S.; Jenssen, J. R.; Radler, E.; Fabris, D., *J. Org. Chem.* 1995, 60, 4167–4176. (b) Tirumala, S.; Davis, J. T., *J. Am. Chem. Soc.* 1997, in press.
18. The oligonucleotide d($T_4isoG_4T_4$) also forms quartets in the presence of $Na^+$; Seela, F.; Wei, C.; Melenewski, A., *Nucleic Acids Res.* 1996, 24, 4940–4945.
19. Cesium-133 NMR has been used to study $Cs^+$ coordination by ionophores, see: (a) Mei, E.; Dye, J. L.; Popov, A. I., *J. Am. Chem. Soc.* 1976, 98, 1619–1620. (b) Mei, E.; Popov, A. I.; Dye, J. L., *J. Am. Chem. Soc.* 1977, 99, 6532–6536. (c) Kauffmann, E.; Dye, J. L.; Lehn, J. M.; Popov, A. I., *J. Am. Chem. Soc.* 1980, 102, 2274–2278. (d) Bauer, W., *Mag. Res. Chem.* 1991, 29, 494–499. (e) Assinus, R.; Böhmer, V.; Harrowfield, J. M.; Oden, M. I.; Richmond, W. R.; Skelton, B. W.; White, A. H., *J. Chem. Soc. Dalton Trans.* 1993, 2427–2433.
20. Wehrli, F. W., *J. Magn. Reson.* 1977, 25, 575–580.
21. Bull, T. E.; Forsen, S.; Turner, D. L., *J. Chem. Phys.* 1979, 70, 3106–3111.
22. (a) Cram, D. J., *Angew. Chem. Int. Ed. Engl.* 1986, 25, 1039–1057. (b) Cram, D. J., *Angew. Chem. Int. Ed. Engl.* 1988, 27, 1009–1020.
23. The $Cs^+$ selectivity for isoG isopropylidene 1 is remarkable considering that related G tetramers, both in nucleosides and in oligonucleotides, are $K^+$ selective: (a) Pinnavaia, T. J.; Marshall, C. L.; Mettler, C. M.; Fisk, C. L.; Miles, T.; Becker, E. D., *J. Am. Chem. Soc.* 1978, 100, 3625–3627. (b) Hardin, C. C.; Watson, T.; Corregan, M.; Bailey, C., *Biochemistry* 1992, 31, 833–841.
24. "Thermodynamic and Kinetic Data for Cation-Macrocycle Interaction." Izatt, R. M.; Bradshaw, J. S.; Nielsen, S. A.; Lamb, J. D.; Chri-istensen, J.; *Chem. Rev.* 1995, 85, 271–339.
25. Seela, F.; Frölich, T., Helv. Chim. Acta, 1994, 77, 399.

What is claimed is:

1. An ionophore comprising a plurality of monomers, wherein each monomer is noncovalently bound to another monomer;
    wherein each monomer is 5'-(t-butyl-dimethylsilyl)-2',3'-O-isopropylidene-isoguanosine;
    wherein the ionophore is capable of forming a complex with a cation selected from the group consisting of $Cs^+$, $Ag^+$, $Hg^{30\ 2}$, $Pb^{+2}$ and $Cd^{+2}$.
2. The ionophore of claim 1, wherein each monomer is bound to another monomer by a hydrogen bond.
3. The ionophore of claim 1, wherein the ionophore comprises a plurality of identical monomers.
4. The ionophore of claim 1, wherein the ionophore comprises four monomers.
5. The ionophore of claim 1, wherein the ionophore comprises eight monomers.
6. The ionophore of claim 1, wherein the cation is $^{137}Cs^+$.
7. The ionophore of claim 1, wherein the binding affinity of the ionophore for $Cs^+$ is greater than the binding affinity of the ionophore for $Na^+$ or $K^+$.
8. The ionophore of claim 1, wherein the ionophore is capable of spontaneously assembling in a solution comprising the plurality of monomers.
9. A complex comprising an ionophore and an ion, wherein the ionophore comprises a plurality of monomers, and each monomer is noncovalently bound to another monomer;
    wherein each monomer is 5'-(t-butyl-dimethylsilyl)-2',3'-O-isopropylidene-isognosine 5'-(t-butyl-dimethylsilyl)-2',3'-O-isopropylidene-thio-isoguanosine.
10. The complex of claim 9, wherein each monomer is bound to another monomer by a hydrogen bond.
11. The complex of claim 9, wherein the ionophore comprises a plurality of identical monomers.
12. The complex of claim 9, wherein the ionophore comprises a plurality of identical monomers.
13. The complex of claim 9, wherein the ionophore comprises four monomers.
14. The complex of claim 9, wherein the ionophore comprises eight monomers.
15. The complex of claim 9, wherein the ionophore is capable of forming a complex with a cation.
16. The complex of claim 15, wherein the cation is $Cs^+$, $Na^+$, $K^+$, $Ag^+$, $Hg^{+2}$, $Pb^{+2}$, or $Cd^{+2}$.
17. The complex of claim 16, wherein the cation is $^{137}Cs^+$.
18. The complex of claim 16, wherein the binding affinity of the ionophore for $Cs^+$ is greater than the binding affinity of the ionophore for $Na^+$ or $K^+$.
19. The complex of claim 9, wherein the ionophore is capable of spontaneously assembling in a solution comprising the plurality of monomers.
20. An ionophore comprising a plurality of monomers, wherein each monomer is noncovalently bound to another monomer;
    wherein each monomer is 5'-(t-butyl-dimethylsilyl)-2',3'-O-isopropylidene-thio-isoguanosine;
    wherein the ionophore is capable of forming a complex with a cation selected from the group consisting of $Cs^+$, $Ag^+$, $Hg^{+2}$, $Pb^{+2}$ and $Cd^{+2}$.
21. The ionophore of claim 20, wherein each monomer is bound to another monomer by a hydrogen bond.
22. The ionophore of claim 20, wherein the ionophore comprises a plurality of identical monomers.
23. The ionophore of claim 20, wherein the ionophore comprises four monomers.
24. The ionophore of claim 20, wherein the ionophore comprises eight monomers.
25. The ionophore of claim 20, wherein the cation is $^{137}Cs^+$.
26. The ionophore of claim 20, wherein the binding affinity of the ionophore for $Cs^+$ is greater than the binding affinity of the ionophore for $Na^+$ or $K^+$.
27. The ionophore of claim 20, wherein the ionophore is capable of spontaneously assembling in a solution comprising the plurality of monomers.

28. An ionophore comprising a plurality of monomers, wherein each monomer is noncovalently bound to another monomer;
  wherein each monomer is 2',3'-Di-O-acetyl-5'-(t-butyl-dimethylsilyl)-isoguanosine;
  wherein the ionophore is capable of forming a complex with a cation selected from the group consisting of $Cs^+$, $Ag^+$, $Hg^{+2}$, $Pb^{+2}$ and $Cd^{+2}$.

29. The ionophore of claim 28, wherein each monomer is bound to another monomer by a hydrogen bond.

30. The ionophore of claim 28, wherein the ionophore comprises a plurality of identical monomers.

31. The ionophore of claim 28, wherein the ionophore comprises four monomers.

32. The ionophore of claim 28, wherein the ionophore comprises eight monomers.

33. The ionophore of claim 28, wherein the cation is $^{137}Cs^+$.

34. The ionophore of claim 28, wherein the binding affinity of the ionophore for $Cs^+$ is greater than the binding affinity of the ionophore for $Na^+$ or $K^+$.

35. The ionophore of claim 28, wherein the ionophore is capable of spontaneously assembling in a solution comprising the plurality of monomers.

36. A method for forming a complex comprising an ionophore and an ion,
  wherein the ionophore comprises a plurality of monomers, and each monomer is noncovalently bound to another monomer;
  wherein the method comprises adding the plurality of monomers to a solution containing the ion, thereby forming the complex;
  wherein each monomer is 5'-(t-butyl-dimethylsilyl)-2',3'-O-isopropylidene-isoguanosine or 5'-(t-butyl-dimethylsilyl)-2',3'-O-isopropylidene-thio-isoguanosine or 2',3'-Di-O-acetyl-5'-(t-butyl-dimethylsilyl)-isoguanosine.

37. A micelle comprising a plurality of ionophores, wherein each ionophore comprises a plurality of monomers, each monomer comprises a hydrophobic moiety, and each monomer is noncovalently bound to another monomer;
  wherein each monomer has the following structure:

[Structure of monomer with NH2, purine base attached to ribose with RO- group and isopropylidene protection]

wherein R is H or $-SiR''_3$, where R'' is a hydrocarbon $(CH_2)_m CH_3$ or an ester $C=O(CH_2)_n CH_3$, wherein m and n are independently 0–22.

38. The micelle of claim 37, wherein each monomer is bound to another monomer by a hydrogen bond.

39. The micelle of claim 37, wherein the ionophore comprises a plurality of identical monomers.

40. The micelle of claim 37, wherein the ionophore comprises four monomers.

41. The micelle of claim 37, wherein the ionophore comprises eight monomers.

42. The micelle of claim 37, wherein the ionophore is capable of forming a complex with a cation.

43. The micelle of claim 42, wherein the cation is $Cs^+$, $Na^+$, $K^+$, $Ag^+$, $Hg^{+2}$, $Pb^{+2}$, or $Cd^{+2}$.

44. The micelle of claim 43, wherein the cation is $^{137}Cs^+$.

45. The micelle of claim 43, wherein the binding affinity of the ionophore for $Cs^+$ is greater than the binding affinity of the ionophore for $Na^+$ or $K^+$.

46. The micelle of claim 37, wherein the ionophore is capable of spontaneously assembling in a solution comprising the plurality of monomers.

47. A method for removing an ion from a solution comprising:
  (a) adding a plurality of monomers to the solution, thereby forming a complex comprising an ionophore and the ion;
    wherein the ionophore comprises the plurality of monomers, and each monomer is noncovalently bound to another monomer; and
  (b) removing the complex from the solution, thereby removing the ion from the solution;
    wherein each monomer is 2'-(t-butyl-dimethylsilyl)-2',3'-O-isopropylidene-isoguanosine or 5'-(t-butyl-dimethylsilyl)-2',3'-O-isopropylidene-thio-isoguanosine or 2',3'-Di-O-acetyl-5'-(t-butyl-dimethylsilyl)-isoguanosine.

48. A method for removing an ion from an aqueous solution comprising:
  (a) adding a plurality of monomers to the solution, thereby forming a composition comprising a micelle and the ion,
    wherein the micelle comprises a plurality of ionophores, each ionophore comprises a plurality of monomers, each monomer comprises a hydrophobic moiety, each monomer is noncovalently bound to another monomer, and the ion is bound to one of the ionophores; and
  (b) removing the composition from the solution, thereby removing the ion from the solution;
    wherein each monomer has the following structure:

[Structure of monomer with NH2, purine base attached to ribose with RO- group and isopropylidene protection]

wherein R is H or $-SiR''_3$, where R'' is a hydrocarbon $(CH_2)_m CH_3$ or an ester $C=O(CH_2)_n CH_3$, wherein m and n are independently 0–22.

49. The method of claim 48, wherein the composition is removed from the solution by ultrafiltration.

* * * * *